United States Patent [19]

Yen

[11] Patent Number: 5,616,311
[45] Date of Patent: Apr. 1, 1997

[54] NON-CROSSLINKED PROTEIN PARTICLES FOR THERAPEUTIC AND DIAGNOSTIC USE

[75] Inventor: Richard C. K. Yen, Glendora, Calif.

[73] Assignee: Hemosphere, Inc., Irvine, Calif.

[21] Appl. No.: 212,546

[22] Filed: Mar. 14, 1994

Related U.S. Application Data

[63] Continuation-in-part of Ser. No. 69,831, Jun. 1, 1993, abandoned, and Ser. No. 959,560, Oct. 13, 1992, Pat. No. 5,308,620, which is a continuation-in-part of Ser. No. 641,720, Jan. 15, 1991, abandoned.

[51] Int. Cl.$^6$ .............................. A61K 51/08; A61K 9/50; B01J 13/08; C12N 11/02
[52] U.S. Cl. .................. 424/1.33; 424/1.29; 424/1.37; 424/484; 424/499; 424/2.14; 424/2.21; 424/213.3; 424/213.33; 428/402.2; 428/402.24; 435/177; 935/54
[58] Field of Search .................. 264/4.3; 427/213.33, 427/2, 2.14, 2.21, 3, 213.3; 428/402.2, 402.24; 424/1.29, 1.33, 1.37, 484, 499; 514/832, 965; 935/54; 435/177

[56] References Cited

U.S. PATENT DOCUMENTS

| | | | |
|---|---|---|---|
| 3,565,559 | 2/1971 | Sato et al. | 428/402.2 X |
| 3,663,686 | 5/1972 | Grotenhuis et al. | 424/1.37 X |
| 4,107,288 | 8/1978 | Oppenheim et al. | 424/499 |
| 4,115,534 | 9/1978 | Ithakissios | 428/402.24 X |
| 4,147,767 | 4/1979 | Yapel, Jr. | 424/499 |
| 4,325,937 | 4/1982 | Spence et al. | 424/16 |
| 4,357,259 | 11/1982 | Senyei et al. | 264/4.3 |
| 4,410,507 | 10/1983 | Chia et al. | 424/1.1 |
| 4,818,542 | 4/1989 | DeLuca et al. | 424/491 |
| 4,822,535 | 4/1989 | Ekman et al. | 264/4.3 |
| 4,921,705 | 5/1990 | Arai et al. | 424/450 |
| 4,963,367 | 10/1990 | Ecanow | 424/484 X |
| 5,049,322 | 9/1991 | Devissaguet et al. | 264/4.1 |
| 5,069,936 | 12/1991 | Yen | 427/213.33 |
| 5,104,674 | 4/1992 | Chen et al. | 426/573 |
| 5,149,540 | 9/1992 | Kunihiro et al. | 424/489 |
| 5,206,023 | 4/1993 | Hunziker | 424/484 X |
| 5,308,620 | 5/1994 | Yen | 424/484 |
| 5,374,441 | 12/1994 | Gibson et al. | 426/656 |

*Primary Examiner*—Richard D. Lovering
*Attorney, Agent, or Firm*—Townsend & Townsend & Crew

[57] ABSTRACT

Albumin particles in the nanometer and micrometer size range in an aqueous suspension are rendered stable against resolubilization without the aid of a crosslinking agent and without denaturation, by the incorporation of hemoglobin in the particle composition. Particles which are primarily hemoglobin in the nanometer and micrometer size range in an aqueous suspension are rendered stable against aggregation by the incorporation of either albumin, surface active agents or gelatin.

26 Claims, No Drawings

NON-CROSSLINKED PROTEIN PARTICLES FOR THERAPEUTIC AND DIAGNOSTIC USE

CROSS REFERENCE TO RELATED APPLICATIONS

This application is a continuation-in-part of application Ser. No. 08/069,831, filed Jun. 1, 1993, now abandoned. This application is also a continuation-in-part of application Ser. No. 07/959,560, filed Oct. 13, 1992, now U.S. Pat. No. 5,308,620, which is a continuation-in-part of application Ser. No. 07/641,720, filed Jan. 15, 1991, now abandoned.

BACKGROUND OF THE INVENTION

Therapeutic drugs are typically administered orally or by intramuscular, subcutaneous, intraperitoneal, or intravenous injections. Intravenous injection is the most direct means of administration and results in the fastest equilibration of the drug with the blood stream. Drugs injected intravascularly reach peak serum levels within a short time, however. Toxic effects can result from such high serum levels, especially if the drug is given as a bolus injection. To avoid such high concentrations, drugs can be administered slowly as a continuous drip. This however requires prolonged nursing care and, in some cases, hospitalization which itself entails high cost. To avoid this, efforts have been made to develop means of administering drugs within stable carriers which allow bolus intravenous injections but provide a gradual release of the drugs inside the vasculature.

The reticuloendothelial system (RES) directs drugs preferentially to the liver and spleen, and its uptake of a carrier thus interferes with the distribution of the drug to other parts of the body. If however the careers are small enough so that the phagocytic cells such as macrophages do not preferentially ingest them, the carriers would escape the RES long enough to perform other tasks. If the carriers also contain antibodies or other ligands on their surfaces which specifically bind to antigenic sites or specific receptors, these antibodies or ligands will direct the drugs to specific cell types containing these sites or receptors. This would result in a higher concentration of the drug near the surfaces of the targeted cells without a higher risk of systemic side effects.

Entrapment of useful agents serves useful purposes in other medical applications as well. Tiny air bubbles, for example, are useful in ultrasonography, where they are used to provide strong contrast to blood vessels and organs traversed by the bubbles. If the bubbles are injected through a peripheral vein, however, they must travel through the right heart, the pulmonary vasculature and then the left heart before they can reach to the other internal organs. Since the bubbles are inherently unstable, they are not able to remain small enough for effective ultrasonographic contrast by the time the intended organs are reached. Entrapment of small air bubbles in small particulate carriers would allow the bubbles to serve their intended function even after long distances of travel within the intravascular compartment.

Similar advantages by using small particulate carriers for contrast material for CAT scans and nuclear magnetic resonance (NMR) scans. Abnormally high concentrations of contrast material at an injection site which might lead to false interpretation of the results could be avoided by administration of the contrast material as an agent retained in a particulate carrier to be released later at the site of the organ of interest.

Oxygen is another vital biological molecule that can be carried within a particulate carrier if the carrier contains hemoglobin. While hemoglobin molecules in large amounts are toxic to the human body, entrapment of hemoglobin within a particulate carrier will reduce its toxicity to vital organs while permitting it to deliver oxygen.

To summarize, stable porous and membraneless carriers which deliver biological agents to sites within the body offer many advantages. The two major approaches of particulate carriers in the prior art are liposomes and microspheres.

In liposomes, a shell is formed by a lipid layer or multiple lipid layers surrounding a central hydrophilic solution containing the medication. The lipid layers are inherently unstable and much research went into stabilizing them during the manufacturing process. In addition, the lipid layer(s) may serve as a barrier to diffusion of certain molecules. It is difficult for a hydrophilic substrate to diffuse through the hydrophobic layers into the interior of the liposomes, or conversely, for the drugs to be released without physical destruction of the lipid layer(s).

Microspheres, in contrast to liposomes, do not have a surface membrane or a special outer layer to maintain their intactness. Most microspheres are more or less homogenous in structure. To maintain the stability of the microspheres, manufacturing procedures in the prior art include a cross-linking process to stabilize the microspheric mass. The cross-linking agent however alters the chemical nature of the natural biological molecule, which may render the resultant product antigenic to the injected host. An anaphylactic reaction to such a newly created antigenicity is unpredictable and potentially dangerous.

Various drugs such as aspirin and non-steroidal antiinflammatory drugs can affect platelet enzymes, which are important components in the circulation of blood within the body. These drugs can thus render the platelets ineffective in hemostasis. Other conditions like cancer or its treatments, including bone marrow transplants, also produce periods of thrombocytopenia which further aggravates the patient's condition. Trauma and surgical operations can lead to open blood vessels which leak not only erythrocytes, but also platelets. These and other conditions can lead to a weak platelet function and consequently impaired circulation.

While this can be remedied by platelet transfusion, certain problems can arise. These include immunization, bacterial and viral transmission, unavailability of platelets in the resuscitation facility because of short shelf-life, and high cost. Attempts to synthesize particulates that can serve as platelet substitutes are disclosed by Agam, G., et al., "Erythrocytes with covalently bound fibrinogen as a cellulare replacement for the treatment of thrombocytopenia," *Eur. J. Clin. Invest.* 22(2):105–112 (1992), and Coller, B. S., et al., "Thromboerythrocytes. In vitro studies of a potential autologous, semi-artificial alternative to platelet transfusions," *J. Clin. Invest.* 89(2):546–555 (1992).

It was known that during activation of platelets, fibrinogen molecules become bound to the surface of platelets. The cell recognition sequence within the fibrinogen molecules contains the sequence "arginine-glycine-aspartic acid (RGD)". Agam, et al. and Coller, et al. demonstrated that erythrocytes with covalently bound fibrinogen and various lengths of RGD, respectively, behaved as activated platelets in the presence of the host's natural platelets and can assist hemostasis.

These "thromboerythrocytes" are expected to have problems similar to those related to the transfusion of erythrocytes:

(a) the erythrocytes from which the final products are made have to be cross-matched to the recipient patient's blood type;

(b) despite sensitive detection assays on the erythrocyte donor, there is no good way of assuring the absence of recent viral infection and viral inactivation on whole erythrocyte preparations are not practical;

(c) the shelf-life of the product is limited by the storage time of erythrocytes; and (d) leakage of hemoglobin after injection of thromboerythrocytes may further aggravate the patient's condition from the problems associated with free hemoglobin infusions.

There is a need for platelet substitutes that do not have these problems.

Literature of potential relevance to the present invention is as follows.

U.S. Pat. No. 4,107,288, Oppenheim, et al., Aug. 15, 1978, for "Injectable Compositions, Nanoparticles Useful Therein, and Process of Manufacturing Same" discloses a process of making microspheres of cross-linked macromolecules by using cross-linking agents such as an aldehyde hardening agent (glutaraldehyde cited as an example). In addition to the hardship in controlling the sizes of the microspheres formed, the Oppenheim process also produces many aggregations which are very undesirable for the purpose of an in vivo medication carrier.

U.S. Pat. No. 4,269,821, Kreuter, et al., May 26, 1981, for "Biological Material" discloses processes for the preparation of submicroscopic particles of a physiologically acceptable polymer associated with a biologically active material by using a cross-linking agent such as a polymerisable material soluble in a liquid medium (methyl methacrylate as an example).

U.S. Pat. No. 3,663,685, Evans et al., May 16, 1972, for "Biodegradable Radioactive Particles" (hereafter "Evans") discloses a method of preparing biodegradable radioactive particles by using heated water-oil solutions.

Widder, et al., "Magnetically Responsive Microspheres and Other Carriers for the Biophysical Targeting of Antitumor Agents", *Advances in Pharmacology and Chemotherapy* 16:213–271 (1979) disclose emulsion polymerization methods of preparation of albumin microspheres (pages 233–235) and preparation of magnetically responsive albumin microsphere (pages 241–250). The methods essentially involve emulsification and heat denaturation of a water-oil solution to produce and stabilize microspheres. The authors also state that for heat sensitive drugs the microspheres are stabilized by chemical cross-linking.

To summarize this literature, typical prior art processes require irradiation, heat, or reaction with a cross-linking agent to polymerize the "monomers" (which are the individual protein molecules such as human serum albumin or gelatin molecules) to convert them to stable particles. Prior art methods which use heat to cross-link and stabilize the protein involve irreversible denaturation of the proteins which renders them "foreign" to the host body.

U.S. Pat. No. 5,049,322, Devissaguet, et al., Sep. 17, 1991 discloses a method of producing a colloidal system containing 150–450 nm particles by dissolving a protein ingredient in a solvent and adding ethanol or mixture of ethanol containing surfactant. Devissaguet does not disclose adding a second protein ingredient. Devissaguet discloses a process of producing colloidal spheres which have a distinct "wall" (column 2, line 25) or "layer" (column 8, line 33) of substance A which is different from the "core" of substance B (column 8, line 18), where the substance B may be a biologically active substance. This disclosure requires that the wall material and the core material both be present in a first liquid phase, which is then added to a second liquid phase that is a non-solvent for both materials. The resulting product is not homogeneous, and relies on the wall for its particle integrity.

Albert L. Lehninger, *Biochemistry: The Molecular Basis of Cell Structure and Function* (1972) discloses that ethanol as a solvent can decrease the ionization of proteins and therefore promote their coalescence and produce "colloidal suspensions". Lehninger does not disclose a special method of preparing colloidal suspensions, but rather generally a method of promoting protein coalescence by using ethanol, "[s]ince a decrease in dielectric constant increases the attractive force between two opposite charges, ethanol decreases the ionization of proteins and thus promotes their coalescence" (page 134, lines 21 through 25, citations omitted). Lehninger has defined the process of "coalescence" as a process leading to "insoluble aggregates" (page 133, lines 31 through 35).

"Remington's Pharmaceutical Sciences", 7th ed. (1985) discloses some general knowledge of "colloidal dispersions". Remington teaches that adding surfactant "stabilizes the dispersion against coagulation" (page 286, column 2, lines 59 and 60), where the surfactant molecules "arrange themselves at the interface between water and an organic solid or liquid of low polarity in such a way that the hydrocarbon chain is in contact with the surface of the solid particle or sticks inside the oil droplet while the polar bead group is oriented towards the water phase" (page 286, column 2, lines 30 through 35). Remington does not specially disclose the use of any particular protein molecules such as globin as the primary protein.

SUMMARY OF THE INVENTION

It has now been discovered that protein particles in the nanometer and micrometer size range, suspended in an aqueous medium, can be made stable against resolubilization (i.e., prevented from redissolving) upon storage, dilution and dialysis, by the inclusion of certain noncrosslinking additives, and that noncrosslinking additives can also reduce or eliminate the tendency of protein particles to aggregate in aqueous suspensions. In particular, particles of non-crosslinked and non-denatured albumin in a suspension are stabilized against resolubilization by the inclusion of hemoglobin in the particle mass, and particles of hemoglobin are stabilized against aggregation by either albumin, surface active agents or gelatin.

A convenient method of forming the particles of either protein is by adding a water-soluble lower alkyl alcohol to an aqueous solution of the protein. Upon formation of the particles, the solution turns turbid. To facilitate the formation of a monodisperse suspension, a surface active agent is preferably included in the original aqueous solution. Once the alcohol has been added and turbidity appears, the suspension may be diluted in an alcohol-free aqueous medium to lower the alcohol content, dialyzed against an aqueous medium to remove the surfactant, or both. Even if neither dilution or dialysis is performed and the particle suspension is administered as formed, a similar effect occurs when the suspension is administered to a patient where it combines with the patient's serum or other bodily fluids. In any case, both dilution and dialysis raise the tendency of the particles to return to solution. In a laboratory vessel, resolubilization is evident when the turbidity disappears and is replaced once again by a clear solution. The additive prevents this from happening without the need for crosslinking. The benefits of the particulate form are thus retained without the need for a crosslinking reaction or the danger of an irreversibly crosslinked particle.

Aggregation of the particles arises in some cases immediately upon their formation and, in some cases, upon dialysis or storage for several hours. Aggregated particles are often too large to be administered effectively, and when close control of the particle size is desired, this is defeated by aggregation. The discovery that aggregation can be avoided by the inclusion of the additives listed above therefore adds a further benefit to the benefits achieved by the elimination of crosslinking.

This invention therefore permits the formation of albumin and hemoglobin particles in the nanometer and micrometer size range, in a form closer to their natural form than the forms of the prior art. The particles thus constitute a more closely controlled agent for in vivo administration, either for their own administration or as a vehicle for other therapeutic or diagnostic agents, with greater ease and assurance of clearance from the body after their period of usefulness. These and other features and advantages of the invention will be apparent from the description which follows.

DETAILED DESCRIPTION OF THE INVENTION AND PREFERRED EMBODIMENTS

The protein particles which are the subject of this invention are monodisperse particles, generally spherical in shape. The term "monodisperse" as used herein denotes discrete single particles which are individually suspended in the aqueous suspension and are neither attached nor adhered to other particles, as distinct from aggregates or aggregated particles, which are groups of two or more, and as many as a hundred or more, such particles adhering to each other by surface interaction or attraction, the aggregates themselves being suspended in the medium in the same manner as the monodisperse particles. While large aggregates can be discerned by the naked eye, a microscope is generally required to differentiate mid-size to small aggregates from monodisperse particles.

The size range of the particles of the present invention extends into both nanometer and micrometer ranges. In general, particles of interest will primarily range from about 50 to about 5000 nanometers in diameter, in monodisperse form. The appropriate or optimal size range for particular uses of the particles or methods of administration will vary with the use or method.

The aqueous medium in which the particles are formed is a homogeneous, water-containing liquid, which may also contain additional components such as surface active agents, buffering agents and inorganic ions. Aqueous media of particular interest in the context of this invention are distilled or deionized water, normal saline and hypotonic saline. In preferred embodiments of the invention, the aqueous medium in which the particles are formed further includes the alcohol which induces the turbidity, the alcohol being fully miscible with the water in the medium to result in a homogeneous continuous phase. In most applications of the invention, the particles will constitute at least about 1.0 g per liter of the suspension, preferably from about 1.0 g per liter to about 150 g per liter, and in many applications at least about 3.0 g per liter, and preferably from about 5.0 g per liter to about 50 g per liter.

In embodiments of the invention in which the suspension is subjected to dilution in, or dialysis against, a second aqueous medium, the second aqueous medium will also be a water-containing liquid, most likely containing neither alcohol nor surfactants. The second aqueous medium is alcohol-free, and is preferably a biological fluid, a fluid similar in composition to a biological fluid, or a fluid which is compatible with a biological fluid. Compatible fluids are those which do not cause adverse physiological effects upon administration. Examples are water, normal saline, and 5% aqueous human serum albumin (HSA).

Dilution may be done to varying degrees, although in most cases the amount of aqueous medium added will result in a volume increase of at least about 50%. The invention is particularly effective when dilutions are performed by adding an equal volume of aqueous medium (100% volume increase) or greater.

The alcohol referred to above is a lower alkyl alcohol, preferably either methanol, ethanol, n-propanol, isopropanol or n-butanol. Among these alcohols, ethanol and n-butanol are particularly preferred. When included, the alcohol is present in an amount sufficient to induce turbidity in the initial aqueous solution of the protein, and preferably to cause precipitation of all protein dissolved in the solution. In most applications, this amount will fall within the range of about 5% to about 80% by volume of the aqueous medium, and preferably from about 10% to about 50%.

The primary protein component of the particles of interest in the present invention is either albumin, hemoglobin or both, neither of which are either denatured or crosslinked. For particles containing albumin, the albumin may be any of the various known types of albumin, the choice being governed by the route or method of administration to the patient. Serum albumin, particularly human serum albumin, is preferred. Hemoglobin may likewise be used in any of its various forms, including stroma-free human adult hemoglobin, fetal hemoglobin, polymerized hemoglobin, pyridoxylated hemoglobin, methemoglobin, and hemoglobin produced by recombinant DNA techniques. Human hemoglobin is preferred, particularly normal adult human hemoglobin.

The surfactants used in certain embodiments of the invention are anionic water-soluble surfactants, preferably sodium or potassium alcohol sulfates. Particularly preferred are sodium or potassium $C_6$–$C_{16}$ alkyl sulfates and sodium or potassium $C_8$–$C_{14}$ alkyl sulfates. Sodium lauryl sulfate and sodium tetradecylsulfate are the most preferred.

The amount of surfactant used in these embodiments may vary depending on the other system parameters. For albumin-based particles where the particles are formed as a suspension in a first aqueous medium, then diluted by addition of a second aqueous medium, best results will be obtained using at least about 1.0 g of surfactant per liter of the suspension prior to dilution or dialysis. Preferably, the surfactant constitutes from about 0.5 g to about 5 g per liter of the suspension, particularly when the suspension contains at least about 15 g of particles per liter of suspension. For hemoglobin-based particles where the surfactant serves as a stabilizer against aggregation, best results are usually obtained with the surfactant at a concentration of at least about 0.1 g per liter of the suspension, prior to dilution if any. Preferred suspensions will contain from about 0.1 to about 10.0 g of surfactant per liter of suspension, and the most preferred will contain from about 0.1 to about 1.0 g of surfactant per liter of suspension.

The gelatin used in certain embodiments of the invention may be gelatin from any of the various known sources, in water-soluble form. Both gelatin A and gelatin B are included. Like the surfactant, the amount of gelatin may vary depending on the other system parameters. As a stabilizer to prevent aggregation of hemoglobin-based particles, best results are usually obtained using gelatin at a concentration of at least about 0.1 g per liter of the suspension prior to dilution. Preferred suspensions will contain from about 0.1 to about 10.0 g of gelatin per liter of suspension, and the most preferred will contain from about 0.1 to about 1.0 g of surfactant per liter of suspension.

In those embodiments in which hemoglobin serves as an additive to albumin to stabilize the albumin against resolubilization, the hemoglobin is preferably incorporated into the bulk of the particle as the particle is being precipitated from the aqueous solution. This is accomplished by dissolving the hemoglobin in the initial aqueous solution together with the albumin, and precipitating both as homogeneous particles upon the addition of the alcohol.

The amount of hemoglobin used in these embodiments may vary depending on the other system parameters, but in most cases best results will be obtained using at least about 1% hemoglobin by weight relative to the total of albumin and hemoglobin. Preferred amounts fall within the range of about 1% to about 70%, more preferred being about 1% to about 30%, and most preferred being about 1% to about 10%.

In those embodiments in which albumin serves as an additive to hemoglobin to stabilize the hemoglobin against aggregation, the two are combined in the same way, and the amount used may also vary over a wide range. In most cases, the amount of albumin will range from about 5% to about 75% by weight of the total of albumin and hemoglobin, although preferred amounts range from about 5% to about 30%, and most preferred from about 5% to about 20%.

The following examples are offered solely for purposes of illustration, and are intended neither to limit nor to define the invention.

EXAMPLE 1

This example illustrates the synthesis of particles of human serum albumin (HSA), followed by dilution in either water or normal saline, the particles being formed without the inclusion of hemoglobin as a stabilizer against resolubilization upon dilution, but with the use of sodium lauryl sulfate (SLS) to prevent aggregation of the particles.

The HSA was prepared by diluting stock HSA (25% in normal saline) in distilled water to 80 mg/mL. Mixtures of this solution were then prepared by combining it with water and SLS in the amounts shown in Table I, followed by the addition of ethanol. As shown in the table, turbidity resulted in each tube, with the particles in tubes 30 and 31 (containing 2 mg/mL and 1 mg/mL, respectively, of the SLS based on the solution prior to the addition of the ethanol) being monodisperse and those in tube 32 (lacking SLS) being aggregated. The table also shows that upon dilution of the tubes with equal volumes of distilled water or normal saline buffer, the contents of tubes 30 and 31 red, dissolved into a clear solution within one hour.

These results indicate that a stabilizer such as hemoglobin is needed for HSA particles to prevent redissolving of the particles upon dilution, and a surfactant is needed to prevent the particles from aggregating.

TABLE I

HSA Particles with Surfactant but no Hb

| Tube No. | Tube Contents (balance: water to achieve total volume of 1.0 mL before addition of alcohol) | | | Size (and Condition) of Particles Formed (μM) | Effect of Dilution |
|---|---|---|---|---|---|
| | HSA (mL at 80 mg/mL) | SLS (mL at 8 mg/mL) | Ethanol (mL) | | |
| 30 | 0.25 | 0.250 | 0.8 | 0.1 (monodisperse) | redissolves |
| 31 | 0.25 | 0.125 | 0.8 | 0.05 (monodisperse) | redissolves |
| 32 | 0.25 | 0.000 | 0.8 | (aggregated) | |

EXAMPLE 2

This example illustrates the synthesis of albumin (HSA) particles with sodium tetradecyl sulfate (STS) to prevent the particles from aggregating, and the effects of including varying amounts of hemoglobin (Hb) as a stabilizer.

A series of mixtures were prepared in test tubes as listed in Table II, in the manner described in the previous examples. A minimal amount of ethanol was then added to each test tube to produce turbidity. The turbid suspensions were the placed in dialysis bags, then dialyzed against normal saline at least 100 fold in volume. The condition of the suspensions during dialysis is shown in the last column of the table, the contents of tube 33 turned clear within two hours, while the contents of the other tubes remained turbid during three days of dialysis. This indicates that the inclusion of as little as 1.48% of hemoglobin (on a weight basis based on total protein) is sufficient to increase the stability of the HSA particle.

TABLE II

HSA With Varying Amounts of Hb

| Tube No. | Tube Contents (balance: water to achieve total volume of 1.0 mL before addition of alcohol) | | | | | Condition of Particle Suspension During Dialysis |
|---|---|---|---|---|---|---|
| | HSA (mL at 80 mg/mL) | Hb (mL at 3 mg/mL) | Hb (weight % of total protein) | STS (mL at 8 mg/mL) | Ethanol (mL) | |
| 33 | 0.25 | 0.0 | 0.0 | 0.25 | 0.8 | clear within 2 hours |
| 34 | 0.25 | 0.1 | 1.48 | 0.25 | 0.8 | turbid for 3 days |
| 35 | 0.25 | 0.2 | 2.91 | 0.25 | 0.4 | turbid for 3 days |
| 36 | 0.25 | 0.3 | 4.31 | 0.25 | 0.3 | turbid for 3 days |
| 37 | 0.25 | 0.4 | 5.66 | 0.25 | 0.2 | turbid for 3 days |

EXAMPLE 3

This example illustrates the incorporation of a therapeutic drug into albumin particles, and also compares albumin and albumin/hemoglobin particles in terms of stability relative to re-solubilization.

Doxorubicin (ADR, purchased from Adria Laboratories, Inc., Columbus, Ohio, U.S.A.) was reconstituted with water to a final concentration of 0.3 mg/mL. Using this solution, a series of mixtures were prepared as listed in Table III, containing either HSA alone or an HSA/Hb combination with sodium tetradecyl sulfate (STS) surfactant. The alcohol, which was either isopropanol ("i-PrOH") or ethanol ("EtOH") as indicated, was then added with rapid shaking. Red particles were observed in each of the tubes.

The contents of the tubes were then diluted with an equal part of either water or normal saline buffer. As the table indicates, the particles in the preparations of HSA without hemoglobin (tubes 103, 104, 105 and 106) redissolved within one hour to form a clear red solution. The particles in the preparations which contained both HSA and hemoglobin did not redissolve, instead remaining intact for at least 24 hours.

larger yet aggregated, each aggregate containing thousands of spheres.

These observations indicate that raising the concentration of the surfactant results in the formation of larger particles which eventually form aggregates as the concentration is increased further.

TABLE IV

HSA Particles With Varying Amounts of Surfactant
(No Dilution or Dialysis)

Tube Contents (balance: water; total volume 5 mL before addition of alcohol)

| Tube No. | HSA (mL at 60 mg/mL) | SLS (mg/mL at 2.5 mL) | Ethanol (mL) | Size and Condition of Particles Formed (µm) |
|---|---|---|---|---|
| 46 | 2.5 | 6 | 5.5 | 0.8; monodisperse |
| 47 | 2.5 | 10 | 5.5 | 1.2; monodisperse |
| 48 | 2.5 | 14 | 5.5 | 1.5–2.0; aggregated |

TABLE III

HSA Particles vs. HSA/HB Particles - Drug Included

Tube Contents (balance: water to achieve total volume of 0.85 mL per tube (Tubes 101–102) or 1.0 mL per tube (Tubes 103–106) before addition of alcohol)

| Tube No. | HSA (mL at 80 mg/mL) | Hb (mL at 63 mg/mL) | STS (mL at 8 mg/mL) | Doxorubicin (mL at 0.3 mg/mL) | Alcohol (mL) | Time for Re-solubilization Upon Dilution |
|---|---|---|---|---|---|---|
| 101 | 0.1 | 0.25 | 0.1 | 0.25 | 0.20 (i-PrOH) | >24 hours |
| 102 | 0.1 | 0.25 | 0.0 | 0.25 | 0.35 (i-PrOH) | >24 hours |
| 103 | 0.25 | none | 0.25 | 0.25 | 0.80 (EtOH) | <1 hour |
| 104 | 0.25 | none | 0.20 | 0.25 | 0.80 (EtOH) | <1 hour |
| 105 | 0.25 | none | 0.15 | 0.25 | 0.80 (EtOH) | <1 hour |
| 106 | 0.25 | none | 0.10 | 0.25 | 0.80 (EtOH) | <1 hour |

EXAMPLE 4

This example illustrates variations in the amount of surfactant present in an HSA particle forming solution, and the effect of these variations on the size and condition of the particles formed.

Mixtures were prepared as listed in Table IV. The surfactant was sodium lauryl sulfate (SLS), and its concentration in the forming solution after having been combined with the HSA was 3.0, 5.0 and 7.0 mg/mL of the forming solution. After five minutes of equilibration, 5.5 mL of ethanol was added to each test tube, and the contents of the tubes were agitated. The contents of the test tubes were then immediately examined under phase microscopy. As noted in the table, tubes 47 and 48 were observed to contain monodisperse particles, with the particles in tube 48 being larger than those of tube 47, while the particles in tube 48 were even

EXAMPLE 5

This example illustrates the use of varying mounts of alcohol in the inducement of particle formation of particles containing human serum albumin stabilized with hemoglobin, and the effects of these varying amounts on the size and condition of the particles.

Mixtures were prepared as listed in Table V. The surfactant was sodium lauryl sulfate and the alcohol was ethanol. The amount of ethanol added ranged from 0.50 to 0.66 mL per tube, compared with a volume of 1.32 mL of the aqueous solution prior to the addition of the ethanol. The results, as shown in the table, indicate that when a critical amount of the alcohol is exceeded, by even a small amount, the particles assumed the form of aggregates rather than monodisperse spheres.

TABLE V

Use of Varying Amounts of Alcohol to Induce Turbidity

| | Tube Contents (balance: water; total volume: 1.32 mL before addition of alcohol) | | | | |
|---|---|---|---|---|---|
| Tube No. | HSA (mL at 250 mg/mL) | Hb (mL at 63 mg/mL) | SLS (mL at 9 mg/mL) | Ethanol (mL) | Size and Condition of Particles Formed ($\mu$m) |
| 52 | 0.2 | 1 | 0.12 | 0.50 | <0.1; monodisperse |
| 53 | 0.2 | 1 | 0.12 | 0.55 | 0.1; monodisperse |
| 54 | 0.2 | 1 | 0.12 | 0.58 | 0.1; monodisperse |
| 55 | 0.2 | 1 | 0.12 | 0.62 | 0.2; monodisperse |
| 56 | 0.2 | 1 | 0.12 | 0.66 | small aggregates |

EXAMPLE 6

This example illustrates the effect of variations in osmolarity on the synthesis of particles of human serum albumin. The osmolarities ranged from from zero, i.e., a sodium-free (hypotonic) medium, to a level below that of normal saline. The varying amounts were achieved by preparing a stock solution of HSA in normal saline and diluting this solution with water before combining it with an aqueous surfactant solution. The ratio of HSA to sodium ion thus remained constant. (At an HSA concentration of 46 mg/mL, the corresponding sodium ion concentration was 27.6 milliequivalents per mL.) The sodium-free medium was obtained by extensively dialyzing the HSA stock solution against distilled water before use.

Diluted HSA and diluted surfactant stock solutions were combined as shown in Tables VI through IX. To achieve turbidity (particle formation), a minimum amount of methanol was added to the combined mixtures of Tables VI and VII, and a minimum of ethanol was added to those of Tables VIII and IX. The existence of aggregation is indicated in each table by the symbol "×", while the formation of monodisperse particles is indicated variously by letter codes.

The data indicates that with methanol to induce turbidity, all tests with sodium ion present resulted in aggregated particles (Table VI), down to an osmolarity as low as 27.6 milliequivalents of sodium per mL. With no sodium ions present (Table VII), however, useful nonaggregated particles were achieved at HSA concentrations as high as 110 mg/mL in conjunction with STS concentration of 7.7 mg/mL. As the concentration of STS was increased further, aggregates resulted, as expected from the preceding examples.

When ethanol was used to induce turbidity, the tests with sodium ion present (Table VIII) indicated that the highest concentration of HSA that could result in monodisperse particles was 148 mg/mL, in conjunction with STS at a concentration as low as 1.4 mg/mL. Here again, raising the STS concentration further resulted in aggregate formation. Tests conducted in the absence of sodium ion (Table IX) resulted in particles of extremely small sizes up to an HSA concentration of 110 mg/mL and an STS concentration of 2.3 mg/mL. With STS at concentrations which were either too low (0.8 mg/mL) or too high (7.4 mg/mL), aggregates were formed.

The data further indicate that a low ionic strength (as exemnplified by the use of dialyzed HSA) allows a higher concentration of HSA to be used (compare Tables VI and VII), but STS concentrations are best within a narrow range. The choice of alcohol affected the results as well—with non-dialyzed HSA, no useful particles were achieved with methanol at an STS concentrations of 2.7 mg/mL and an HSA concentration of 74 mg/mL. Monodisperse particles were achieved however with ethanol at HSA concentrations up to 148 mg/mL and STS at 1.4 mg/mL. Also, the particle size achieved with methanol was smaller than that achieved with ethanol.

TABLE VI

Use of Non-Dialyzed HSA (Na$^+$ Ion Present) in Methanol to Show Effect of High Osmolarity

| HSA* (mg/mL) | Presence or Absence of Aggregation (X = Aggregation Present) STS (mg/mL)*: | | | | | | |
|---|---|---|---|---|---|---|---|
|  | 11.5 | 7.3 | 6.4 | 5.5 | 4.5 | 3.6 | 2.7 |
| 110 | X | X | X | X | X | X | X |
| 102 | X |   |   |   |   |   |   |
| 92  | X | X | X | X | X | X | X |
| 83  | X |   |   |   |   |   |   |
| 74  | X | X | X | X | X | X | X |
| 64  | X |   |   |   |   |   |   |
| 55  | X |   |   |   |   |   |   |
| 46  | X |   |   |   |   |   |   |

*Equal volumes of HSA and STS solutions were mixed together to result in the concentrations shown, before the addition of alcohol.

TABLE VII

Use of Dialyzed HSA (Na$^+$ Ion Removed) in Methanol to Show Effect of Low Osmolarity

| HSA* (mg/mL) | Condition of Spheres (X = Aggregated; C = Monodisperse, <0.05 $\mu$m; D = Monodisperse, <0.1 $\mu$m) STS* (mg/mL): | | | | | | | | |
|---|---|---|---|---|---|---|---|---|---|
|  | 11.5 | 9.1 | 8.2 | 7.7 | 7.3 | 6.4 | 5.5 | 4.5 | 3.6 | 2.7 |
| 110 | X |   |   | C |   |   |   |   |   |   |
| 102 | X |   |   | C |   |   |   |   |   |   |
| 92  | X |   |   | X |   |   |   |   |   |   |
| 83  | X |   |   | D |   |   |   |   |   |   |
| 74  | X | X | X | X | X | D | X | D | D | D |
| 64  | X |   |   | C |   |   |   |   |   |   |
| 55  | X |   |   | C |   |   |   |   |   |   |
| 46  | X |   |   | C |   |   |   |   |   |   |

*Equal volumes of HSA and STS solutions were mixed together to result in the concentrations shown, before the addition of alcohol.

TABLE VIII

Use of Non-Dialyzed HSA (Na Ion Present) in Ethanol
to Show Effect of High Osmolarity Condition of Spheres
(X = Aggregated; A = Monodisperse, 0.5–0.8 μm;
B = Monodisperse, 1–2 μm)

| HSA (mg/mL) | STS (mg/mL)*: 24.5 | 18.2 | 13.6 | 9.1 | 7.4 | 5.5 | 3.6 | 1.8 | 1.4 | 0.9 | 0 |
|---|---|---|---|---|---|---|---|---|---|---|---|
| 227 | X | X | X | X | X | X | X | X | X | X | X |
| 216 |   |   |   |   |   |   |   |   | X |   |   |
| 204 |   |   |   |   |   |   |   |   | X |   |   |
| 193 |   |   |   |   |   |   |   |   | X |   |   |
| 185 |   |   |   | X |   |   |   |   |   |   |   |
| 182 |   |   |   |   |   |   |   |   | X |   |   |
| 170 |   |   |   |   |   |   |   |   | X |   |   |
| 159 |   |   |   |   |   |   |   |   | X |   |   |
| 148 |   |   |   |   |   |   |   |   | B |   |   |
| 136 |   |   |   | X |   |   |   |   | B |   |   |
| 125 |   |   |   |   |   |   |   |   | B |   |   |
| 113 |   |   |   |   |   |   |   |   | B |   |   |
| 102 |   |   |   |   |   |   |   |   | B |   |   |
| 91  |   |   |   | X |   |   |   |   | B |   |   |
| 79  |   |   |   |   |   |   |   |   | B |   |   |
| 74  |   |   |   |   |   |   |   |   | A |   |   |
| 56  |   |   |   |   |   |   |   |   | A |   |   |
| 37  |   |   |   |   |   |   |   |   | B |   |   |

*Equal volumes of HSA and STS solutions were mixed together to result in the concentrations shown, before the addition of alcohol.

TABLE IX

Use of Dialyzed HSA (Na Ion Removed) in Ethanol
to Show Effect of Low Osmolarity Condition of Spheres
(X = Aggregated; E = Monodisperse, 0.1 μm;
F = Monodisperse, 1–3 μm; G = Monodisperse,
0.3–0.5 μm; H = Monodisperse, <0.5 μm;
I = Monodisperse, 0.8–1.0 μm)

| HSA (mg/mL) | STS (mg/mL)*: 9.1 | 8.2 | 7.4 | 6.4 | 5.5 | 4.5 | 3.6 | 2.7 | 2.3 | 1.4 | 0.8 |
|---|---|---|---|---|---|---|---|---|---|---|---|
| 110 |   |   |   |   |   |   |   |   | H | F | X |
| 101 |   |   |   |   |   |   |   |   | E | E | X |
| 92  |   |   |   |   |   |   |   |   | G | H | X |
| 83  |   |   |   |   |   |   |   |   | G | H | X |
| 74  | X | X | X | E | F | F | G | G | E | E | X |
| 64  |   |   |   |   |   |   |   |   | I | H | X |

*Equal volumes of HSA and STS solutions were mixed together to result in the concentrations shown, before the addition of alcohol.

EXAMPLE 7

The purpose of this example is to illustrate that the formation of Hb/HSA particles does not rely on the interaction of the heme groups of hemoglobin with the HSA molecules.

The HSA molecule is known to have many sites suitable for the binding of heme groups. This example therefore involves the incubation of the HSA with hematin to saturate all of these sites prior to formation of the particles. The hematin used was bovine hematin (Sigma Chemical Company, St. Louis, Mo., U.S.A.), and various proportions relative to the HSA were used—12.5, 10.0, 7.5, 5.0, 2.5 and 0 mg/mL, with 25 mg/mL of HSA.

An aliquot of 0.05 mL was taken from each of these six tubes and added to a second set of six tubes containing 5 mg Hb per 0.95 mL normal saline. Subsequently, 0.10 mL of n-butanol was added to the mixture and the tubes shaken to produce turbidity. Immediately after turbidity appeared, another 0.05 mL of HSA was added to each tube, this HSA having been pre-incubated with the respective concentration of hematin to eliminate the possibility of post-synthesis aggregation of the particles due to insufficient HSA.

Monodisperse particles were formed in all six tubes, stable relative to aggregation and remaining so upon washing in hypotonic 0.009% saline. The conclusion is that the pre-saturation of heme-binding sites on the HSA molecules does not prevent the formation of the particles.

EXAMPLE 8

This example compares Hb-stabilized HSA particles which are crosslinked with Hb-stabilized HSA particles which are not crosslinked, and also illustrates the incorporation of DNA into HSA-based particles. The crosslinking agent was glutaraldehyde.

A mixture was prepared consisting of 0.4 mL of HSA (250 mg/mL) and 0.1 mL of stroma-free human hemoglobin (60 mg/mL, containing more than 10% as methemoglobin). The hemoglobin thus constituted 5.7 weight percent relative to the total of HSA and hemoglobin. To this was added 0.5 mL of a DNA solution (1.0 μg dissolved in normal saline) with agitation. Ethanol (200 proof) was then added dropwise until turbidity appeared (approximately 0.4 mL). Examination by microscopy revealed that the particles were 0.2 μm in size. The suspension was then divided in two. One of the two halves was combined with 0.1 mL of a glutaraldehyde solution (0.01% in normal saline), and the other with 0.1 mL of normal saline as a control. After five minutes, both halves were further combined with 3 mL of normal saline to dilute the particle suspension.

Assay of the DNA contents of the two mixtures showed that in each case, more than 90% of the DNA was trapped inside and on the surfaces of the particles. After removal of the DNA in the supernatant, both particle preparations, each containing DNA, were incubated in DNA-free media overnight. Assays then conducted showed that no DNA had been lost from the particles. Attempts to degrade the entrapped DNA resulted in the release of less than 5% of the particle-bound DNA, indicating that most of the DNA resided in the particle interiors. Furthermore, the similarity in results between the two preparations indicated that the stability of particles prepared without the glutaraldehyde crosslinking agent was equivalent to that of the crosslinked particles.

EXAMPLE 9

This example is a further comparison of Hb-stabilized HSA particles which are crosslinked with Hb-stabilized HSA particles which are not crosslinked, and also illustrates the adherence of DNA and RNA to the surfaces of HSA-based particles.

A mixture was prepared consisting of 0.4 mL of HSA (250 mg/mL) and 0.1 mL of stroma-free human hemoglobin (60 mg/mL, containing more than 10% as methemoglobin), the hemoglobin thus constituting 5.7 weight percent relative to the total of HSA and hemoglobin. Ethanol (200 proof) was then added dropwise until turbidity appeared (approximately 0.4 mL). Examination by microscopy revealed that the particles were 0.2 μm in size. The suspension was then divided in two. One of the two halves was combined with 0.1 mL of a glutaraldehyde solution (0.01% in normal saline), and the other with 0.1 mL of normal saline as a control. After five minutes, both halves were dialyzed overnight against normal saline at a volume of 1000-fold to remove the ethanol.

Approximately 0.02 μg of RNA was then mixed with 100 microliters of each suspension, and the particles were then separated from the supernatant by high speed centrifugation. Analysis of the RNA content revealed that about 50% of the RNA had become attached to the surfaces of the preformed particles.

The experiment was then repeated, except that 0.1 μg of DNA was used in place of the RNA. Analysis subsequently revealed that at least 90% of the DNA had become attached to the surfaces of the particles. Again, there was no difference between the two groups in terms of particle stability, indicating that the stability of particles prepared without the glutaraldehyde crosslinking agent was equivalent to that of the crosslinked particles.

EXAMPLE 10

This example illustrates the association of DNA with albumin particles, both by incorporation into the particle bulk and by adherence to the particle surface.

Mixtures were prepared by combining 20 μL of HSA (250 mg/mL) with 5 μL of hemoglobin solution (60 mg/mL) and 20 μL of DNA solution (containing 12.5 μg of DNA). To the mixture was then added 18 μL of ethanol, resulting in 63 μL of a particle suspension. Centrifugation and analysis of the supernatant revealed that 90% of the DNA originally added was contained in the particles, and that the particle yield was approximately 20%. Thus, at least 11.25 μg of DNA can be captured by 1.06 mg of the particles. It is believed that up to one mg of DNA can be captured by one mg of particles.

The experiment was repeated, except that the DNA solution was added after the ethanol had been added and the suspension formed rather than before. Centrifugation and analysis of the supernatant again revealed that 90% of the DNA originally added had adhered to the particles, again with a particle yield of approximately 20%. Thus, at least 11.25 μg of DNA can be captured by 1.06 mg of the particles, and potentially up to one mg of DNA per one mg of particles, both by incorporation into the particles as they are being formed and by adherence to particles already formed.

To confirm that the DNA incorporated into the interior of the particles was protected from degradation by an endonuclease, 10 μL aliquots of suspensions of both types of particles were incubated with an endonuclease preparation for thirty minutes at 37° C. The suspensions were then centrifuged to separate the supernatant from the particles. The supernatants were then analyzed by gel electrophoresis to reveal migration patterns consistent with those of DNA fragments known to result from digestion of the same DNA with the same enzyme. The pellets were then treated by layering 50 μL of ethylenediaminetetraacetic acid (EDTA) solution (50 mM) onto the pellets carefully without disturbing the pellets. The EDTA was applied in this manner to deactivate any endonuclease remaining in the pellets, and thereby avoid the degradation of DNA which would be released when the particles were subsequently redissolved. A weak alkaline solution (0.003N NaOH, 5 μL in volume) was then added to each of the two pellets to form turbid suspensions, which were then incubated for ten minutes at 37° C. A solution of sodium dodecyl sulfate (SDS, 5 μL, 10 mg/mL) was then added to each suspension, and both then became clear, indicating that the particles had redissolved. Gel electrophoresis of the released DNA gave migration patterns that were identical to those of DNA molecules which had not been incorporated into or adhered to the particles.

These results indicate that regardless of whether the DNA is present in the bulk of the particle or merely attached to the particle surface, the DNA is not susceptible to enzymatic degradation. Large amounts of DNA can be protected by either of these methods. It is possible that the restriction sites were covered by the protein molecules and therefore inaccessible to the endonucleases, or that the association of the DNA molecules with the particles caused stereohindrance which prevented the orientation necessary for the endonuclease or the DNA molecules for purposes of enzymatic digestion. Alternatively, the association of the DNA with the particles may have rendered co-factors needed by the degradative process unavailable or inaccessible. In any event, the DNA incorporated into the particle bulk or adhering to the particle surface was not damaged in any way and could be released in intact form from the particles.

EXAMPLE 11

This example illustrates the synthesis of HSA particles slightly larger in size than those of Example 10, and the effects of the inclusion of increasing amounts of surfactant. Dilution of the particle suspension was not performed in this experiment. The surfactant once again was sodium lauryl sulfate (SLS).

Solutions were prepared as listed in Table X, exclusive of the ethanol. After five minutes of equilibration, the ethanol was added to each tube. Aliquots of the contents of each tube were examined under phase microscopy, with results as indicated in the table. These results are consistent with those of Example 10 by showing that higher concentrations of surfactant resulted in larger particles. As the concentration is further increased, however, the particles aggregate, as observed in tube 148.

TABLE X

| HSA Particles Formed With Increasing Amounts of Surfactant | | | |
|---|---|---|---|
| Tube Contents (balance: water; total volume: 5.0 mL before addition of alcohol) | | | Size and Condition of |
| Tube No. | HSA (mL at 60 mg/mL) | SLS (mg/mL of 2.5 mL) | Ethanol (mL) | Particles Formed (μm) |
| 146 | 2.5 | 6 | 5.5 | Monodisperse; 0.8 |
| 147 | 2.5 | 10 | 5.5 | Monodisperse; 1.2 |
| 148 | 2.5 | 14 | 5.5 | Aggregated; 1.5–2.0 |

EXAMPLE 12

This example illustrates the synthesis of hemoglobin particles in normal saline buffer and the effects of including varying amounts of human serum albumin as a stabilizer.

A series of mixtures were prepared in test tubes as listed in Table XI, by first combining the hemoglobin, the human serum albumin and the normal saline, and then quickly adding isopropanol with vigorous mixing. Within ten seconds of vigorous mixing, turbidity appeared in each tube.

The contents of each tube were examined by phase contrast microscopy, which revealed monodisperse (i.e., non-aggregated) particles of homogeneous size in tubes 1 to 5, and remained so when stored at room temperature for at least four days. In contrast, aggregated particles were seen in tubes 6, 7 and 8, and sediment was observed in these tubes within hours of synthesis.

The isopropanol was then removed from the particle suspensions by placing aliquots of the suspensions in separate dialysis bags and dialyzing the aliquots against normal saline at least 100 fold in volume. The particles from tubes 1 to 5 neither aggregated nor dissolved even after four days of dialysis. In contrast, large aggregates remained inside the dialysis bags containing material from tubes 6 to 8.

The data indicate that a minimum of about 5% HSA by weight, based on the total weight of protein, is needed for stable monodisperse particles which are primarily hemoglobin. The data also indicate that progressively smaller particles are achieved by increasing the HSA-to-hemoglobin ratio.

TABLE XI

Hb With Varying Amounts of HSA
Tube Contents (balance: normal saline; total volume: 3 mL per tube before addition of alcohol)

| Tube No. | Hb (mL at 60 mg/mL) | HSA (mg/ mL at 0.1 mL) | HSA (as % of total protein) | Iso-propanol (mL) | Particles Formed Size (μm) | Condition After Dialysis |
|---|---|---|---|---|---|---|
| 1 | 0.225 | 200 | 59.8 | 0.75 | 0.8 | mono-disperse |
| 2 | 0.225 | 100 | 42.6 | 0.75 | 1.0 | mono-disperse |
| 3 | 0.225 | 50 | 27.0 | 0.75 | 1.2 | mono-disperse |
| 4 | 0.225 | 25 | 15.6 | 0.75 | 1.5 | mono-disperse |
| 5 | 0.225 | 12 | 8.2 | 0.75 | 1.5 | mono-disperse |
| 6 | 0.225 | 6 | 4.2 | 0.75 | 2–4 | aggregates |
| 7 | 0.225 | 3 | 2.2 | 0.75 | 2–4 | aggregates |
| 8 | 0.225 | 0 | 0 | 0.75 | 2–4 | aggregates |

EXAMPLE 13

This example illustrates the synthesis of hemoglobin particles, followed by dilution in either water or aqueous HSA but without dialysis, and the use of sodium tetradecyl sulfate (STS) or gelatin to prevent aggregation of the particles.

The STS used was Sotradecol 3%, a form of STS approved for intravenous injection by the U.S. Food and Drug Administration. Although STS produces irritation in veins at 3% concentration, this does not occur at lower concentrations. Gelatin solutions were prepared by dissolving gelatins in distilled water at a concentration of 2% (weight/volume). The alcohols used were ethanol (EtOH), n-butanol (BuOH) and isopropanol (i-PrOH).

A series of mixtures were prepared in test tubes as listed in Table XII, by first combining all ingredients except the alcohol, then quickly adding the alcohol with agitation. Turbidity appeared within ten seconds in all test tubes. Examination by phase microscopy revealed that the particles in tubes 9 through 17 were monodisperse and homogeneous in size (typically less than 0.2 micron in diameter), and remained so for at least eight days without aggregation or the formation of sediment. In tubes 18 through 20, by contrast, large aggregates were visible, even with the unaided eye, demonstrating that the stabilizers were effective in preventing aggregation.

Aliquots of all tubes were serially diluted in either distilled water or 5% HSA solution in normal saline (to simulate the intravascular environment) until the original suspension became at least 1000 times less concentrated. Turbidity was still visible in all tubes, indicating that the particles, whether monodisperse or aggregated, were stable to dilution.

TABLE XII

Hb With Stabilizers to Prevent Aggregation
Tube Contents (balance: water to achieve total volume of 3 mL before addition of alcohol)

| Tube No. | Hb (mL at 60 mg/mL) | STS (mL at 2.8 mg/mL) | Gelatin (mL at 20 mg/mL) | Alcohol (mL) | Condition of Particles Formed |
|---|---|---|---|---|---|
| 9 | 0.225 | 0.25 | none | 1.10 (EtOH) | mono-disperse |
| 10 | 0.225 | 0.25 | none | 0.20 (BuOH) | mono-disperse |
| 11 | 0.225 | 0.25 | none | 1.00 (i-PrOH) | mono-dispserse |
| 12 | 0.225 | none | 0.1 | 1.25 (EtOH) | mono-disperse |
| 13 | 0.225 | none | 0.1 | 0.20 (BuOH) | mono-disperse |
| 14 | 0.225 | none | 0.1 | 0.75 (i-PrOH) | mono-disperse |
| 15 | 0.225 | 0.25 | 0.1 | 1.23 (EtOH) | mono-disperse |
| 16 | 0.225 | 0.25 | 0.1 | 0.20 (BuOH) | mono-disperse |
| 17 | 0.225 | 0.25 | 0.1 | 1.00 (i-PrOH) | mono-disperse |
| 18 | 0.225 | none | none | 1.20 (EtOH) | aggre-gates |
| 19 | 0.225 | none | none | 0.20 (BuOH) | aggre-gates |
| 20 | 0.225 | none | none | 0.75 (i-PrOH) | aggre-gates |

EXAMPLE 14

This example illustrates the effect of varying the amount of either gel or HSA on the size of hemoglobin particles.

A series of mixtures were prepared in test tubes as listed in Table XIII, by first combining all ingredients except the alcohol, then quickly adding the alcohol (n-butanol) with agitation to produce the turbidity. The suspensions were then diluted over 100 times in distilled water.

Examination by phase microscopy revealed that the particles in the tubes were homogeneous in size in each tube and stable relative to dilution, although of varying sizes from one tube to the next as indicated in Table XIII. The particles in tube 23 were difficult to see under 1000× magnification.

The data indicate that increasing the ratio of gelatin to hemoglobin results in a decrease in the size of the particles. No significant difference, however, was observed in the tubes containing varying amounts of HSA in place of the gelatin. This is in contrast to the results shown in Table XII (Example 12), where isopropanol was used in place of n-butanol and increases in the ratio of HSA to hemoglobin did result in decreases in the particle size.

TABLE XIII

| | Effect of Amount of Gel or HSA on Particle Size | | | | | |
|---|---|---|---|---|---|---|
| | Tube Contents (balance: water to achieve total volume of 3 mL per tube before addition of alcohol) | | | | | |
| Tube No. | Hb (mL at 60 mg/mL) | STS (mL at 2.8 mg/mL) | Gelatin (mL at 20 mg/mL) | HSA (mL at 250 mg/mL) | n-BuOH (mL) | Size of Particles Formed (μm) |
| 21 | 0.225 | 0.25 | 0.10 | none | 0.30 | 0.1 |
| 22 | 0.225 | 0.25 | 0.25 | none | 0.30 | ≈0.05 |
| 23 | 0.225 | 0.25 | 0.50 | none | 0.30 | <<0.05* |
| 24 | 0.225 | 0.25 | none | 0.10 | 0.30 | 0.2 |
| 25 | 0.225 | 0.25 | none | 0.25 | 0.30 | 0.15 |
| 26 | 0.225 | 0.25 | none | 0.50 | 0.30 | 0.2 |

*Particles difficult to see under 1000× magnification.

EXAMPLE 15

This example illustrates how larger hemoglobin particles can be formed by using a higher concentration of hemoglobin in the forming solution.

Mixtures were prepared in test tubes as in Example 14, using HSA exclusively, but with a hemoglobin concentration of 45 mg/mL (mg of hemoglobin per mL of the total aqueous solution prior to addition of the alcohol). This compares with a maximum hemoglobin concentration of 4.5 mg/mL (same units) in Example 14. As a result, the particles in this example (tube nos. 27 through 29) were considerably larger in size, as shown in Table XIV.

TABLE XIV

| | Hb Particles formed at Higher Concentration | | | | |
|---|---|---|---|---|---|
| | Tube Contents (balance: water to achieve total volume of 3 mL per tube before addition of alcohol | | | | Size of |
| Tube No. | Hb (mL at 60 mg/mL) | STS (mL at 2.8 mg/mL) | HSA (mL at 250 mg/mL) | n-Butanol (mL) | Particles Formed (μm) |
| 27 | 2.25 | 0.25 | 0.10 | 0.30 | 1.0–1.2 |
| 28 | 2.25 | 0.25 | 0.25 | 0.30 | 1.0–1.2 |
| 29 | 2.25 | 0.25 | 0.50 | 0.30 | 1.0–1.2 |

EXAMPLE 16

This example illustrates the incorporation of biological agents into hemoglobin particles. Two such agents were used—radioactive iodine (bonded to the hemoglobin) and alkaline phosphatase.

An aliquot of hemoglobin solution was iodinated with Iodine-125 by a standard chloramine-T linking method. The specific activity of the resulting labeled hemoglobin solution was found to be approximately 6 microcuries per mg protein. The conditions of tube 2 in Example 12 were used—i.e., 0.225 mL of Hb at 60 mg/mL, 0.1 mL HSA at 100 mg/mL, 2.675 mL normal saline and 0.75 mL isopropanol—except that the hemoglobin included both radioactive hemoglobin and nonradioactive hemoglobin mixed together. Alkaline phosphatase was incorporated by using a solution of alkaline phosphatase (0.1 mg/mL in normal saline buffer) instead of normal saline buffer.

After the addition of 0.8 mL isopropanol to precipitate the particles and form a suspension, measurements of radioactivity and alkaline phosphatase activity were performed on an aliquot of the suspension. Another aliquot was centrifuged to remove all particles, and the clear supernatant was assayed for radioactivity and alkaline phosphatase activity. It was found that at least 80 percent of the total radioactivity as well as alkaline phosphatase activity had been retained in the particles.

EXAMPLE 17

This example illustrates the synthesis of hemoglobin particles in a hyperosmolar buffer, and the use of sodium tetradecyl sulfate (STS) and gelatin for preventing aggregation of the particles.

A series of mixtures were prepared in test tubes as listed in Table XV. To determine the yield of particles formed by the hemoglobin, the hemoglobin used in these mixtures contained iodine-125 labeled hemoglobin to result in about 5,000 cpm of radioactivity per mg hemoglobin. To achieve hyperosmolarity, a 3× normal saline (465 mM NaCl) buffer with 20 mM sodium phosphate, pH 7.4, with a total osmolarity equal to at least 970 milliosmos was used. The mixtures shown in the table were allowed to equilibrate for at least 5 minutes, after which time the n-butanol was added to each tube and the contents of the tubes were shaken. The tube contents became turbid as a result, and were viewed by phase microscopy, which indicated that the particles in tubes 38 to 42 were monodisperse while those in tubes 43 to 45 were aggregated.

To ascertain the yield of particles, the radioactivity of each particle suspension was first determined, and the particles were then removed by high speed centrifugation for at least twenty minutes. The radioactivity of the supernatant was then determined. The percentage yield of the particles was determined by dividing the difference between the cpm of the whole suspension and that of the supernatant by the cpm of the whole suspension. These determinations indicated that the yield ranged from 73% to 95%.

Aliquots from all tubes were then placed in dialysis bags and dialyzed in normal saline at 100 fold volume. The aliquots from tubes 38 to 42 remained monodisperse, while those from tubes 43 to 45 continued to show aggregates visible to the unaided eye.

Aliquots from all tubes were then diluted at one volume per two volumes of water to produce a final concentration of sodium chloride equivalent to normal saline buffer. Once again, the aliquots from tubes 38 to 42 remained monodisperse, while aggregates were still visible in the aliquots from tubes 43 to 45.

The conclusion from these experiments is that STS alone at the concentration of 0.03 mg per mL of solution (exclusive of the alcohol) was insufficient to prevent aggregation of the hemoglobin particles, although aggregation was prevented by the further inclusion of gelatin at concentrations exceeding 3.6% by weight relative to the hemoglobin (i.e., concentrations exceeding that of Tube No. 43).

TABLE XV

Hb/Gelatin Particles in Hyperosmolar Buffer

Tube Contents (balance: buffer*; total volume: 11 mL before addition of alcohol)

| Tube No. | Hb (mL at 50 mg/mL) | STS (mL at 3.2 mg/mL) | Gelatin (mL at 10 mg/mL) | n-Butanol (mL) | Condition of Particles | | |
|---|---|---|---|---|---|---|---|
| | | | | | As First Formed | After Dialysis | After Dilution |
| 38 | 0.80 | 1.0 | 1.00 | 1.12 | mono-disperse | intact, mono-disperse | intact, mono-disperse |
| 39 | 0.80 | 1.0 | 0.80 | 1.12 | mono-disperse | intact, mono-disperse | intact, mono-disperse |
| 40 | 0.80 | 1.0 | 0.60 | 1.12 | mono-disperse | intact, mono-disperse | intact, mono-disperse |
| 41 | 0.80 | 1.0 | 0.40 | 1.12 | mono-disperse | intact, mono-disperse | intact, mono-disperse |
| 42 | 0.80 | 1.0 | 0.20 | 1.12 | mono-disperse | intact, mono-disperse | intact, mono-disperse |
| 43 | 0.80 | 1.0 | 0.15 | 1.12 | aggregated | intact, aggregated | intact, aggregated |
| 44 | 0.80 | 1.0 | 0.10 | 1.12 | aggregated | intact, aggregated | intact, aggregated |
| 45 | 0.80 | 1.0 | 0.00 | 1.12 | aggregated | intact, aggregated | intact, aggregated |

Buffer: 3 × normal saline (465 mM NaCl) with 20 mM sodium phosphate, pH 7.4 (total osmolarity equal to at least 970 milliosmos).

EXAMPLE 18

This example illustrates variations in the amount of surfactant present in an Hb particle forming solution, and the effect of these variations on the size and condition of the particles formed.

Mixtures were prepared as listed in Table XVI. The surfactant was again sodium lauryl sulfate (SLS), and its concentration in the forming solution after having been combined with the Hb was 0.64, 0.82 and 1.0 mg/mL of the forming solution. After five minutes of equilibration, 0.35 mL of ethanol was added to each test tube, and the contents of the tubes were agitated, then examined under phase microscopy. As noted in the table, tubes 49 and 50 were observed to contain monodisperse particles, with the particles in tube 50 being larger than those of tube 49, while the particles in tube 51 were even larger but were aggregated.

These observations indicate that for hemoglobin as well, raising the concentration of the surfactant results in the formation of larger particles which eventually form aggregates as the concentration is increased further.

TABLE XVI

Hb Particles With Varying Amounts of Surfactant (No Dilution or Dialysis)

Tube Contents (balance: water; total volume 1.1 mL before addition of alcohol)

| Tube No. | Hb (mL at 30 mg/mL) | SLS (mg/mL at 0.1 mL) | Ethanol (mL) | Size and Condition of Particles Formed ($\mu$m) |
|---|---|---|---|---|
| 49 | 1.0 | 7 | 3.5 | 0.1; monodisperse |
| 50 | 1.0 | 9 | 3.5 | 0.2; monodisperse |
| 51 | 1.0 | 11 | 3.5 | 0.3; aggregated |

EXAMPLE 19

This example illustrates the use of different alcohols for inducement of particle formation of Hb/HSA particles.

Mixtures were prepared in test tubes as listed in Table XVIII. The alcohols were added after equilibration of the tube contents, and the tubes were shaken. The tube contents were examined by phase microscopy, and the results were as recorded in the table, indicating that the size of the particles was affected by the choice of alcohol.

TABLE XVII

Effect of Choice of Alcohol on Particle Size

| Tube No. | Hb (mL at 60 mg/mL) | HSA (mL at 250 mg/mL) | STS (mL at 30 mg/mL) | Alcohol (type; mL) | Particle Size (μm) |
|---|---|---|---|---|---|
| 57 | 1.0 | 0.12 | 0.112 | ethanol; 0.462 | 0.05 |
| 58 | 1.0 | 0.12 | 0.112 | i-propanol; 0.462 | 0.5 |
| 59 | 1.0 | 0.12 | 0.112 | n-butanol; 0.462 | 1.5 |

EXAMPLE 20

This example illustrates the synthesis of Hb/HSA particles in the absence of a surfactant, under conditions resulting in particles of up to 4 microns in size, and the effect of adding additional HSA after formation of the particles to adhere to the particle surfaces.

The alcohol used in these experiments was n-butanol, and a preliminary experiment was conducted to ascertain the amount of n-butanol which would produce the highest yield of particles. Each of a series of eight test tubes was charged with 5 mg/mL of Hb and 2.5 mg/mL of HSA. This was followed by the addition of n-butanol in increasing amounts from one tube to the next, the amounts being 0.6, 0.8, 1.0, 1.2, 1.4, 1.6, 1.8 and 2.0 mL, per 10 mL of the protein mixture solution. The tubes were thoroughly shaken to produce turbidity. After one hour, 5 mL of the turbid suspension were removed from each tube and centrifuged to obtain a pellet. The supernatant was then removed without disturbing the pellet, and 5 mL of 0.05N sodium hydroxide was added to the pellet to solubilize the pellet completely for protein analysis. The amount of Hb obtained from the pellet as a percentage of the amount of soluble Hb present before addition of the alcohol was defined as the particle yield. It was found that the yield increased with increasing amounts of n-butanol, and reached a maximum of about 95% when the ratio of n-butanol to protein solution (volume/volume) was 0.14.

This ratio was then used in the next series of tests to explore the conditions suitable for production of large particles in high yield and which remain monodisperse. This series of tests is represented in Table XVIII. Protein solutions were prepared as listed in the table. After the butanol was added, the tubes were capped and shaken upside down three to ten times to produce turbidity. In certain designated tubes as shown in the table, an additional amount of HSA was added immediately after the appearance of turbidity. Phase microscopy was used to evaluate the size and condition of the particles, with the results listed in the last column of the table.

The observations listed in the table indicate a line of demarcation at an Hb volume of 166.7 μL (which corresponds to an Hb concentration of about 5 mg/mL in the protein/saline solution prior to addition of the alcohol), since higher amounts of Hb produced aggregation which was not eliminated by the added HSA. At this concentration of Hb, systems with less than 2.5 mg/mL of HSA (i.e., less than 100 μL at 25 mg/mL in 1 mL total solution; tubes 80–82), formed particles which were initially monodisperse but aggregated within minutes after their formation unless the additional amount of HSA was added immediately after turbidity appeared.

The conclusion to be drawn from these observations is that high yields of Hb/HSA particles can indeed be obtained with a high volume ratio of the alcohol to the protein solution, but that below a certain minimum concentration of HSA in the particles, aggregation of the particles occurs within ten minutes of their formation, and further that this aggregation can be avoided by applying HSA to the exterior of the particles immediately after they are formed. The fact that HSA can be made to adhere to the exterior of these particles after their formation by merely contacting the particles with dissolved HSA suggests that biologically active molecules can be caused to adhere to the particle surfaces in the same way. Examples of such biologically active molecules are homing devices such as antibodies and ligands against certain cell receptors.

The monodisperse particles in the various preparations listed in Table XVIII settled to the bottom of the tubes within one day. The supernatants were then removed by decantation or other conventional means, and the recovered particles were washed several times with either normal saline or distilled water. Examination under phase microscopy indicated that the particle sizes and conditions had not changed, and therefore that stability with respect to both redissolving and aggregation had been maintained.

TABLE XVIII

Stabilizing Influence of Surface-Adhering HSA

| | Tube Contents (balance: normal saline; total volume: 1.0 mL before addition of alcohol) | | | HSA Added After | |
|---|---|---|---|---|---|
| Tube No. | Hb (μL at 30 mg/mL) | HSA (μL at 25 mg/mL) | n-Butanol (μL) | Turbidity (μL at 25 mg/mL) | Size and Condition of Particles Formed (μm) |
| 60 | 16.7 | 0 | 140 | 0 | aggregated |
| 61 | 16.7 | 20 | 140 | 0 | aggregated |
| 62 | 16.7 | 50 | 140 | 0 | monodisperse; 1.0 |
| 63 | 16.7 | 100 | 140 | 0 | monodisperse; 0.8 |
| 64 | 16.7 | 200 | 140 | 0 | monodisperse; 0.4 |
| 65 | 16.7 | 0 | 140 | 100 | monodisperse; 1.0 |
| 66 | 16.7 | 20 | 140 | 80 | monodisperse; 1.0 |
| 67 | 16.7 | 50 | 140 | 50 | monodisperse; 0.8 |
| 68 | 16.7 | 100 | 140 | 0 | monodisperse; 0.8 |
| 69 | 16.7 | 200 | 140 | 0 | monodisperse; 0.4 |
| 70 | 66.7 | 0 | 140 | 0 | aggregated |
| 71 | 66.7 | 20 | 140 | 0 | aggregated |
| 72 | 66.7 | 50 | 140 | 0 | monodisperse; 1.5–2.0 |
| 73 | 66.7 | 100 | 140 | 0 | monodisperse; 1.2–1.5 |
| 74 | 66.7 | 200 | 140 | 0 | monodisperse; 1.0 |
| 75 | 66.7 | 0 | 140 | 100 | monodisperse; 2.0 |
| 76 | 66.7 | 20 | 140 | 80 | monodisperse; 1.0–2.5 |
| 77 | 66.7 | 50 | 140 | 50 | monodisperse; 1.0–1.5 |
| 78 | 66.7 | 100 | 140 | 0 | monodisperse; 1.0 |
| 79 | 66.7 | 200 | 140 | 0 | monodisperse; 1.0 |

TABLE XVIII-continued

| Stabilizing Influence of Surface-Adhering HSA | | | | | |
|---|---|---|---|---|---|
| | Tube Contents (balance: normal saline; total volume: 1.0 mL before addition of alcohol | | | HSA Added After | Size and |
| Tube No. | Hb (μL at 30 mg/mL) | HSA (μL at 25 mg/mL) | n-Butanol (μL) | Turbidity (μL at 25 mg/mL) | Condition of Particles Formed (μm) |
| 80 | 166.7 | 0 | 140 | 0 | aggregated |
| 81 | 166.7 | 20 | 140 | 0 | aggregated |
| 82 | 166.7 | 50 | 140 | 0 | aggregated |
| 83 | 166.7 | 100 | 140 | 0 | monodisperse; 2.0–2.5 |
| 84 | 166.7 | 200 | 140 | 0 | monodisperse; 2.0–2.5 |
| 85 | 166.7 | 0 | 140 | 100 | monodisperse; 2.0–4.0 |
| 86 | 166.7 | 20 | 140 | 80 | monodisperse; 2.0–4.0 |
| 87 | 166.7 | 50 | 140 | 50 | monodisperse; 2.0–3.0 |
| 88 | 166.7 | 100 | 140 | 0 | monodisperse; 2.0–2.5 |
| 89 | 166.7 | 200 | 140 | 0 | monodisperse; 2.0–2.5 |
| 90 | 333.3 | 0 | 140 | 0 | aggregated |
| 91 | 333.3 | 20 | 140 | 0 | aggregated |
| 92 | 333.3 | 50 | 140 | 0 | aggregated |
| 93 | 333.3 | 100 | 140 | 0 | aggregated |
| 94 | 333.3 | 200 | 140 | 0 | aggregated |
| 95 | 333.3 | 0 | 140 | 100 | aggregated |
| 96 | 333.3 | 20 | 140 | 80 | aggregated |
| 97 | 333.3 | 50 | 140 | 50 | aggregated |
| 98 | 333.3 | 100 | 140 | 0 | aggregated |
| 99 | 333.3 | 200 | 140 | 0 | aggregated |

EXAMPLE 21

This example illustrates the incorporation of alkaline phosphatase into Hb/HSA particles and the attachment of hemagglutinin molecules to the surfaces of the particles.

A mixture corresponding to that of tube 87 of Example 20 was prepared, except that the normal saline solution was replaced by the same volume of an alkaline phosphatase enzyme solution in normal saline (1 mg/mL), and the solution added after turbidity appeared was a solution of hemagglutinin molecules at 0.58 mg/mL (Fluogen), all other components and proportions being identical to those of tube 87. After allowing the particles to settle to the bottom of the tube, the supernatant was removed and the particles were washed five times with normal saline to remove all soluble proteins. The particles were then added to (alkaline phosphatase negative) mammalian cells in culture, and observed under a microscope. Within five minutes, particles prepared in the presence of hemagglutinin had become attached to the cell surfaces and could not be rinsed away. In contrast, particles prepared in an identical manner but in the absence of hemagglutinin did not attach to the cells and were readily removed by rinsing the cells. The hemagglutinin molecules had therefore attached themselves to the surfaces of the particles.

Cells with particles adhering to their surfaces were then fixed with a standard fixative and stained with a solution containing compounds that would form a dark purple insoluble stain in reaction with alkaline phosphatase. All particles showed a uniform dark color after the reaction, indicating that the alkaline phosphatase was incorporated uniformly among the particles.

EXAMPLE 22

This example provides a comparison of hemoglobin-based particles with erythrocytes.

The particle preparations of tubes 77 and 87 of Example 20 were repeated but scaled up to 1 liter total volume. The resulting particles were separated by gravity sedimentation, washed three times in normal saline, then sedimented once again. The supernatant was removed by suction, leaving a very dense suspension of particles. The particles in the suspension were analyzed by examination under a hemocytometer after proper dilution to determine the number of particles per mL, and by standard biochemical analysis to determine the amounts of Hb and HSA as percentages of total protein. The results are shown in Table XIX, where they are compared with corresponding values for erythrocyes. The data in the table indicate that the particles had hemoglobin contents comparable to that in human blood.

TABLE XIX

| Comparison of High-Yield Hb/HSA Particles With Erythrocytes | | | |
|---|---|---|---|
| | Erythrocytes | Particles From Tube 87 | Particles From Tube 77 |
| Count (billion/mL) | 3.5–3.9 | 1.1 | 9.0 |
| Mean Diameter (μm) | 7 | 25 | 1.7 |
| Hb as Percent of Total Protein in Sphere | | 87.5 | 96.1 |
| HSA as Percent of Total Protein in Sphere | | 12.5 | 3.9 |
| Hb Concentration in Fluid (g/dL) | 12–16 | 5.9 | 12.8 |
| Total Protein Concentration (Hb + HSA) (g/dL) | | 6.7 | 13.3 |

Particles prepared in accordance with the present invention are useful for a wide variety of purposes.

Hemoglobin-based particles of the present invention are particularly useful for therapeutic administration. In addition to providing a porous structure for drug absorption, hemoglobin molecules can bind oxygen which is the drug of choice for many pathological conditions related to ischemia. Included among such pathological conditions are coronary obstruction, cerebral vascular constriction, pulmonary vascular constriction, peripheral vascular disease and sickle cell crisis. While hemoglobin molecules may be toxic when administered in large amounts, the particles of the present invention retain the great majority of the hemoglobin within their bulk, out of contact with the host's organs. Only those hemoglobin molecules exposed on the particle surface will contact the organs. Accordingly, particles with a high hemoglobin content can mimic erythrocytes and will be less toxic to the host than soluble hemoglobin when used in massive amounts as oxygen carriers.

In addition, hemoglobin particles can serve as carders for blood clot dissolving agents such as urokinase or streptokinase. Injection of particles of a wide size range into patients suffering from acute coronary spasm, thrombosis or embolism can serve a dual function. Particles of about 0.1 micron in size or less will pass through partial occlusions to deliver oxygen to distal sites, while larger particles are retained by the occlusions where they will dissolve the clot and thereby recannulate the coronary vessel.

For both albumin-based and hemoglobin-based particles, additional substances serving a therapeutic or diagnostic function, or both, other than the albumin or hemoglobin, can be entrapped within the particle bulk and carried by the particles to a site for in vivo administration. Examples of classes of such substances are enzymes, amino acids, peptides, nucleic acids, contrast agents and nonmacromolecular therapeutic drugs. A contrast agent of particular interest is technetium. The incorporation of these additional substances is conveniently achieved by combining them with the protein solutions from which the proteins are precipitated to form the particles.

Additional substances can also be attached non-covalently to the exterior surfaces of the particles. Examples of substances which are useful when adhered to the particles in this manner are proteins, immunoglobulins and nucleic acids, as well as molecular species in general which exhibit specific binding to biological molecules such as cell surface receptors. Specific examples of particular interest are fibrinogen and peptides which contain reactive sequences of fibrinogen, such as arginine-glycine-aspartic acid (RGD). Adherence of these substances to the particle surfaces is conveniently achieved by contacting the substances with the particles soon after the particles are formed.

The following is a list of examples of specific substances which can be incorporated into the composition of particles of the present invention.
1. Protein A
2. Concanavalin A
3. IgG
4. hemagglutinin
5. transferrin
6. von-Willebrand factor
7. anti-human factor IX monoclonal antibody
8. anti-CD8 monoclonal antibody
9. goat anti-clathrin
10. fibronectin
11. human fibroblast growth factor-acidic, recombinant
12. human interleukin-2, recombinant
13. anti-human platelet-derived growth factor beta receptor
14. anti-beta-lipoprotein
15. alpha 2-macroglobulin
16. streptokinase
17. anti-progesterone antibody
18. anti-leukotriene B4 antibody
19. CGGRGDF-NH$_2$
20. doxorubicin
21. daunorubicin
22. EDTA-conjugated to HSA
23. DTPA-conjugated to HSA
24. technetium
25. gadolinium
26. HSA conjugated to FITC (Fluorescein Isothiocyanate)
27. HSA conjugated to TRITC (Tetramethylrhodamine B isothiocyanate)
28. HSA conjugated to PE (Phycoerythrin)
29. HSA conjugated to Ferritin
30. HSA conjugated to biotin
31. alkaline phosphatase
32. peroxidase
33. amphotericin B
34. Adjuvant peptide (N-acetylmuramyl-1-alanyl-d-isoglutamine)
35. HIV-1 protease substrate (acetyl-ser-gln-asn-tyr-pro-val-val-amide)
36. Fe$_3$O$_4$ magnetite or magnetic particles
37. cysteine-cyclohexanol conjugate
38. HIV-glycoprotein 120
39. anti-CD4 antibody
40. fibrinogen Albumin-based particles containing Tc99m either in their bulk or on their surfaces are illustrative of the use of these particles as vehicles for specific agents. The incorporation or attachment of Tc99m can be achieved through direct covalent bonding or through a chelating agent. Examples of chelating agents are cysteine-cyclohexanol conjugate and DTPA.

The chelating agent may be pre-bonded to soluble HSA molecules which are then mixed with other HSA molecules during the formation of the original aqueous protein solution. Alternatively, chelating agents may be covalently bonded directly to preformed particles. A third alternative is to add the chelating agent as one of the biological molecules, not covalently bound to any HSA molecules. The chelating agent will then be trapped within the particles or near their surfaces when the particles are formed.

The procedure of binding the Tc99m to the particles, with or without chelating agents, can follow standard nuclear medicine procedures. For example, stannous chloride or other reducing agents (0.01 to 0.3 mg) can be added to approximately 1 mg of particles suspended in a suitable buffer to reduce the sulfhydryl groups in the protein molecules. Sodium pertechnetate Tc99m (5 to 250 millicurie) is then added to the suspension. The excess reducing agent reduces the pertechnetate (TcO$_4^-$) to TcO$_2^-$, which then binds to the sulhydryl group on the protein molecules, or to the sites on the chelating agents designed to bind the TcO$_2^-$. It is expected that more Tc99m binds to particles through chelating agents than without chelating agents.

Alternatively, stannous chloride and lyophilized particles could be stored as a dry powder in the absence of oxidizing agents, to be reconstitued as a suspension by the addition of Tc99m solutions.

The presence of chelating agents has the additional advantage of possibly stabilizing the TcO$_2^-$ before it binds to the protein molecules.

An alternative method would be to allow pertechnetate Tc99m to be reduced by a reducing agent in the presence of a free chelating agent, i.e., one which is not yet associated with the particles, then binding the Tc99m-chelating agent conjugate to the particles.

The particles may alteratively be reduced by a different reducing agent after which they can be purified and stored as a reduced dry (lyophilized) powder, while the pertechnetate would be reduced by a different kind of reducing agent immediately before interaction with the already reduced particles. Due to the short half life of Tc99m, the product which results from the mixing of the pertechnetate-containing liquid with the particle suspension or powder should be ready for injection into a patient within much less than one hour and without the need for other purification. Examples of reducing agents are dithiothreitol, dithioerythritol, ascorbic acid, 2-mercaptoethanol, and pyrophosphate. In addition, the reduced TcO$_2^-$ may first be stabilized by an intermediate product involving D-glucarate.

A wide variety of bioactive molecules can be incorporated within the interior, on the surface, or near the surface of the particles. Combinations of one or more compounds can also be incorporated into a single particle.

Examples of biologically active molecules that can be incorporated include, but not limited to: drugs, biologically active peptides, polypeptides, carbohydrates, lipids, lipoproteins, glycoproteins, enzymes, ligands, receptors, radioactive compounds, fluorescent or excitable compounds, imaging materials, oxygen-carrying materials, toxins, anti-toxins, neurologically active materials, chemotherapeutic agents, chelating compounds, nucleotides, nucleoside, nucleic acids, polynucleotides, antibiotics, magnetic materials, and nutrients. Further examples are subunits or fragments of these molecules, as well as analogs of the molecules, their competitors, inhibitors, and antagonists, antibodies against them, antibodies against antibodies against them, receptors to which they will bind, anti-sense entities (whether in the form of RNA, DNA or even protein forms), and the genes from whose information they are derived.

The following are examples of biologically active molecules which can be incorporated in the manner described above.

Lipids methanoic, ethanoic, propanoic, butanoic, pentanoic, hexanoic, heptanoic, octanoic, nonanoic, decanoic, undecanoic, dodecanoic, tridecanoic, tetradecanoic, pentadecanoic, hexadecanoic, heptadecanoic, octadecanoic, nonadecanoic, eicosanoic, heneicosanoic, docosanoic, tricosanoic, tetracosanoic, pentacosanoic, hexacosanoic, heptacosanoic, octacosanoic, nonacosanoic, triacontanoic, hentriacontanoic, 10-undecenoic, cis-9-tetradecenoic, trans-9-tetradecenoic, cis-10-pentadecenoic, cis-9-hexadecenoic, trans-9-hexadecenoic, cis-10-heptadecenoic, cis-6-octadecenoic, trans-6-octadecenoic, cis-7-octadecenoic, cis-9-octadecenoic, trans-9-octadecenoic, cis-11-octadecenoic, trans-11-octadenenoic, cis-12-octadecenoic, cis-13-octadecenoic, cis-12-hydroxy-9-octadecenoic, trans-12-hydroxy-9-octadecenoic, cis-9,12-octadecadienoic, trans9,12-octadecadienoic, 9,11(10,12)-octadecadienoic, cis-6,9,12-octadecatrienoic, cis-9,12,15-octadecatrienoic, cis-6,9,12,15-octadecatetraenoic, cis-10-nonadecenoic, cis-5-eicosenoic, cis-8-eicosenoic, cis-11-eicosenoic, cis-13-eicosenoic, cis-11, 14eicosadienoic, cis-5,8,11-eicosatrienoic, 5,8,11-eicosatriynoic, cis-8,11,14-eicosatrienoic, cis-11,14, 17-eicosatrienoic, cis-5,8,11,14-eicosatetraenoic, 5,8, 11,14-eicosatetraynoic, cis-5,8,11,14,17-eicosapentaenoic, cis-13-docosenoic, trans-13-docosenoic, cis-13,16-docosadienoic, cis-13,16,19-docosatrienoic, cis-7,10,13,16-docosatetraenoic, cis-4, 7,10,13,16,19-docosahexaenoic, cis-15-tetracosenoic acids.

Lectins

Abrus precatorius (Agglutinin, Abrin A toxin, Abrin C toxin), Agaricus bisporus, Anguilla anguilla, Arachis hypogaea, Bandeiraea simplicifolla (BS-I, BS-I-B4, BS-I-AB3, BS-I-A2B2, BS-I-A3B, BS-I-A4, BS-II), Bauhinia purpurea, Caragana arborescens, Cicer arietinum, Codium fragile, Concanavalin A, Succinyl-Concanavalin A, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Limulus polyphemus (Bacterial agglutinin), Lycopersicon esculentum, Maclura pomifera, Momordica charantia, Mycoplasma gaillsepticum, Naja mocambique mocambique, Naja naja kaouthia, Perseau americana, Phaseolus coccineus, Phaseolus limensis, Phaseolus vulgaris (PHA-E, PHA-L), Phytolacca americana, Pisum sativum, Pseudmonas aeruginosa PA-I, Psophocarpus tetragonolobus, Ptilota plumosa, Ricinus communis (Toxin, RCA60, Toxin, RCA120), Robinia pseudoacacia, Sambucus nigra, Solanum tuberosum, Sophora japonica, Tetragonolobus purpureas, Triticum vulgaris, Ulex europaeus (UEAI, UEAII), Vicia faba, Vicia sativa, Vicia villosa (A4, B4), Vigna radiata, Viscum album, Wisteria floribunda.

Complement Proteins, Either as Single Proteins or as Combinations of Several Proteins C1q, C2, C3, C4, C5, C6, C7, C8, C9, Properdin factor B.

Spin Labels and Spin Traps

Doxyl Nitroxides, e.g., 3-beta-doxyl-5-alpha-cholestane;

Proxyl Nitroxides, e.g., 3-(4-nitrophenoxycarbonyl)-proxyl;

Tempo Nitroxides, e.g., Tempo;

DL-t-Butyl Nitroxide;

Spin traps: Nitrosobenzene, Nitrosadisulfonic acid, 2-methyl-2-Nitroso-Propane.

Arachidonic Acid Cascade and Related Compounds

HETEs: 5(S)-HETE[5(S)-hydroxy-6-trans-8-cis-11-cis-14-cis-eicosatetraenoic acid]; 11(S)-HETE[11(S)-hydroxy-5-cis-8-cis-12-trans-14-cis-eicosatetraenoic acid]; 12(R)-HETE[12(R)-hydroxy-5-cis-8-cis-10-trans-14-cis-eicosatetraenoic acid]; 12(S)-HETE [12(S)-hydroxy-5-cis-8-cis-10-trans-14-cis-eicosatetraenoic acid]; 15(S)-HETE[15(S)-hydroxy-5-cis-8-cis-11-cis-13-trans-eicosatetraenoic acid];

HPETEs: 5(S)-HPETE[5(S)-hydroperoxy-6-trans-8-cis-11-cis-14-cis-eicosatetraenoic acid]; 12(S)-HPETE[12(S)-hydroperoxy-5-cis-8-cis-10-trans-14-cis-eicosatetraenoic acid]; 15(S)-HPETE[15(S)-hydroperoxy-5-cis-8-cis-11-cis-13-trans-eicosatetraenoic acid];

DiHETEs: 5(S),6(R)-DiHETE[5(S),6(R)-dihydroxy-7-trans-9-trans-11-cis-14-cis-eicosatetraenoic acid]; 5(S), 12(S)-DiHETE[5(S),12(S)-dihydroxy-6-trans-8-cis-10-trans-14-cis-eicosatetraenoic acid]; 5(S),15(S)-DiHETE [5(S),15(S)-dihydroxy-6-trans-8-cis-11-cis-13-trans-eicosatetraenoic acid]

Other Arachidonic Acid Cascade Related Compounds

13-Azaprostanoic acid; Baicalein; 7–7-dimethyleicosadienoic acid; 5,8,11-eicosatriynoic acid; 5,8,11,14-eicosatetraynoic acid; oleoyloxyethyl Phosphocholine; sodium furegrelate; w-3 fatty acids; leukotrienes (LTA4, LTB4, LTC4, LTD4, LTE4); lipoxin (A4, B4), Prostaglandins (A2, B2, D2, E1, E2, F2α, I2, G2, H2); 16-16-Dimethyl-prostaglandin E2; 6-Keto-prostaglandin F1α; 2,3-Dinor 6-ketoprostaglandin F1α; 9,11-Dideoxy-9α, 11α-methanoepoxyprostaglandin-F2α; Carbacyclin; Thromboxanes (CTA2, B2, A2); p-Arbutin; H-Arg-gly-Asp-OH; H-Arg-Gly-Asp-Ser-Pro-Ala-Ser-Ser-Lys-Pro-OH; Ascorbate oxidase; ascorbic acid; asparagine; aspartic acid; arachidonic acid Ion Channel Modulators Amiloride, Baicalein, BAY K 8644, Bepridil, Brevetoxin (PbTx-1, PbTx-2, PbTx3, PbTx-7, PbTx-9), w-Conotoxin GVIA, Conus geographus, Diltiazem, Methoxyverapamil, Nifedipine, Ryanodine, 9,21,-Dehydro-Ryanodine, Saxitoxin, Tetrodotoxin, TMB-8, Toxin II, Verapamil.

Biologically Active Peptides 4-(2-Acetamido-2-deoxy-beta-D-Glucopyranosyl)-N-acetylmuramyl-L-Ala-D-Glu Amide N-Acetyl-Asp-Glu N-Acetyl-Cholecystokinin and its fragments N-Acetyl-Hirudin and its fragments Acetyl-Leu-Leu-Argininal N-Acetyl-Leu-Leu-Methioninal N-Acetyl-Leu-Leu-Norleucinal Acetyl-Met-Asp-Arg-Val-Leu-Ser-Arg-Tyr N-Acetyl-Met-Leu-Phe
N-Acetylmuramyl-D-alanyl-D-isoglutamine
N-Acetylmuramyl-L-alanyl-D-isoglutamine
N-Acetylmuramyl-L-alanyl-L-isoglutamine
N-Acetylmuramyl-Ala-D-isoglutaminyl-Ne-stearoyl-Lys
N-Acetyl-Phe-Nle-Arg-Phe Amide
Acetyl-Renin Substrate Tetradecapeptide
Acetyl-Ser-Asp-Lys-Pro
Acetyl-Ser-Gln-Asn-Tyr
Acetyl-Ser-Gln-Asn-Tyr-Pro-Val-Val Amide
Acetyl-Ser-Tyr-Ser-Met-Glu-His-Phe-Arg-Trp-Gly-Lys-Pro-Val Amide
N-Acetyl-Thr-Ile-Nle-Phe(CH$_2$NH)-Nle-Gln-Arg Amide
ACTH (Adrenocorticotropic Hormone)
Adrenal Cyclase Activating Polypeptide-27
Adrenal Medulla Peptides
Adrenal Peptide E
Adrenocorticotropic Hormone and fragments
Adrenorphin
Adipokinetic Hormone II
Adjuvant Peptide
Ala-Arg-Pro-Gly-Tyr-Leu-Ala-Phe-Pro-Arg-Met Amide
beta-Ala-Arg-Ser-Ala-Pro-Thr-Pro-Met-Ser-Pro-Tyr
Ala-D-gamma-Glu-Lys-D-Ala-D-Ala
Ala-Gly-Cys-Lys-Asn-Phe-Phe-Trp-Lys-Thr-Phe-Thr-Ser-Cys
Ala-Gly-Ser-Glu
Ala-D-isoglutaminyl-Lys-D-Ala-D-Ala
Ala-Leu-Ala-Leu
Ala-Leu-Ile-Leu-Thr-Leu-Val-Ser
Ala-Lys-Pro-Ser-Tyr-Hyp-Hyp-Thr-Tyr-Lys
Ala-Ser-His-Leu-Gly-Leu-Ala-Arg
beta-Ala-Ser-His-Leu-Gly-Leu-Ala-Arg
Ala-Ser-Thr-Thr-Thr-Asn-Tyr-Thr
D-Ala-Ser-Thr-Thr-Thr-Asn-Tyr-Thr Amide
Aldosterone Secretion Inhibiting Factor
Allatotropin
Alytesin
Amastatin
beta-Amyloid and fragments
Angiogenin and fragments
Angiotensin I and analogs
Angiotensin II and analogs
Angiotensin III and analogs
Angiotensin Converting Enzyme Inhibitor
Angiotensinogen and fragments
Angiotonin
Anorexogenic Peptide
Anthranilyl-His-Lys-Ala-Arg-Val-Leu-p-Nitro-Phe-Glu-Ala-Nle-Ser Amide
Antide
Anti-inflammatory Peptide 1
Antipain
Antireproductive Tripeptide
Apamin
Arg-Arg-Leu-Ile-Glu-Asp-Ala-Glu-Tyr-Ala-Ala-Arg-Gly
Arg-Arg-Leu-Ile-Glu-Asp-Asn-Glu-Tyr-Thr-Ala-Arg-Gly
Arg-Arg-Lys-Ala-Ser-Gly-Pro
Arg-Gly-Asp
Arg-Gly-Asp-Ser
Arg-Gly-Asp-Ser-Pro-Ala-Ser-Ser-Lys-Pro
Arg-Gly-Glu-Ser
Arg-Gly-Phe-Phe-Tyr-Thr-Pro-Lys-Ala
Arg-Gly-Pro-Phe-Pro-Ile
Arg-His-Phe
Arg-Lys-Arg-Ala-Arg-Lys-Glu
Arg-Lys-Asp-Val-Tyr
Arg-Lys-Glu-Val-Tyr
Arg-Phe-Asp-Ser
Arg-Pro-Lys-Pro-Gln-Gln-Phe-Phe-Gly-Leu-Met Amide
Arg-Pro-Pro-Gly-Phe-Ser-Pro-Phe-Arg
Arg-Ser-Arg-His-Phe
Arg-Tyr-Leu-Pro-Thr
Arg-Tyr-Val-Val-Leu-Pro-Arg-Pro-Val-Cys-Phe-Glu-Lys-Gly-Met-Asn-Tyr-Thr-Val-Arg
Asn-Ala-Gly-Ala
Asn-Pro-Asn-Ala-Asn-Pro-Asn-Ala
Asn-Pro-Asn-Ala-Asn-Pro-Asn-Ala-Asn-Pro-Asn-Ala
Asp-Ala-Glu-Asn-Leu-Ile-Asp-Ser-Phe-Gln-Glu-Ile-Val
Asp-Arg-Val-Tyr-Ile-His-Pro-Phe-His-Leu
Asp-Leu-Trp-Gin-Lys
Asp-Ser-Asp-Pro-Arg
Atrial Natriuretic Peptide and fragments
Atriopeptins
Auriculin
Avidin
Beauvericin
Bestatin
Biocytin-Neuropeptide Y
Biotin/biotinylated peptides
N-t-BOC-beta-Ala-Trp-Met-Asp-Phe Amide
N-t-BOC-beta-Ala-Trp-Met-beta-(Benzyl)Asp-Phe Amide
N-t-BOC-Gly-Trp-Met-Asp-Phe Amide
N-t-BOCGly-Trp-Met-beta-(benzyl)Asp-Phe Amide
N-t-BOC-Glu-Glu-Ile Methyl Ester
N-t-BOC-Glu-Glu-Leu Methyl Ester
N-t-BOC-Glu-Glu-Val Methyl Ester
N-t-BOC-Lys-Pro-Tyr-Ile-Leu Methyl Ester
N-t-BOC-Met-Asp-Phe Amide
N-t-BOC-Met-Leu-Phe
N-t-BOC-Nle-Leu-Phe
N-t-BOC-Phe-D-Leu-Phe
N-t-BOC-Phe-Leu-Phe-Leu-Phe
N-t-BOC-Trp-Asp-Phe Amide
N-t-BOC-Trp-Met-Asp-Phe Amide
N-t-BOC-Trp-Met-Phe Amide
Bombesin and analogs
Bradykinin and analogs
Bradykinin Potentiator (e.g. 5a, 9a, B, C)
Brain Natriuretic Peptide
Brefeldin A Buccalin
Bursin
Caerulein
Calcitonin
Calcitonin Gene Related Peptide
beta-Calcitonin Gene Related Peptide
Calcitonin Gene Related Peptide fragment 8–37
Calcitonin Precursor Peptide
Calmodulin-Dependent Protein Kinase II (fragment 290–309)
Calpain Inhibitor I
Calpain Inhibitor II
Calpain Inhibitor Peptide
Carassin
N-Carboxymethyl-Phe-Leu
N-([R,S]-2-Carboxy-3-phenylpropionyl)-L-Leucine
Cardioexcitatory Peptide
alpha-Casein and fragments
Beta-Casomorphin
Na-CBZ-Arg-Arg-Pro-Phe-His-Sta-Ile-His-Ne-BOC-Lys Methyl Ester
CBZ-Leu-Val-Gly Diazomethyl Ketone
N-CBZ-D-Phe-Phe-Gly
N-CBZ-Pro-D-Leu
N-CBZ-Pro-Leu-Gly Hydroxamate
CD4 and fragments
Cecropins
Cerebellin
Chemostactic Peptides
Cholecystokinin and fragments
Chorionic Gonadotropin and fragments
Chromostatin-20
Chymostatin
Circumsporozoite (CS) Protein of *Plasmodium falciparum* repetitive sequences
Collagen
Conotoxin GI
μ-conotoxin GIIIB
ω-conotoxin GVIA
α-conotoxin SI
Copper Binding Peptide
Corazonin
Corticotropin A
Corticotropin-Like Intermediate Lobe Peptide
Corticotropin Releasing Factor and analogs
Tyr-Corticotropin Releasing Factor
Corticotropin Releasing Factor Antagonist
C-Peptide and fragments
Cyclic-AMP Dependent Protein Kinase Substrate
Cyclo(7-Aminoheptanoyl-Phe-D-Trp-Lys-Thr[Bzl])
Cyclo(D-Asp-Pro-D-Val-Leu-D-Trp)
Cyclohexylacetyl-Phe-Arg-Ser-Val-Gln Amide
Cyclo(His-Phe)
Cyclo(His-Pro)
Cyclo(Leu-Gly)
Cyclo(Phe-Ser)
Cyclo(Pro-Gly)3
Cyclo(D-Trp-Lys-Thr-Phe-Pro-Phe)
Cyclo(D-Trp-Lys-Thr-Phe-Pro-Tyr)
Cys-Gln-Asp-Ser-Glu-Thr-Arg-Thr-Phe-Tyr
Cys-Ser-Arg-Ala-Arg-Lys-Gln-Ala-Ala-Ser-Ile-Lys-Val-Ala-Val-Ser-Ala-Asp-Arg
Cys-Tyr-Ile-Gln-Asn-Cys-Pro-Arg-Gly Amide
Cys-Tyr-Ile-Gln-Asn-Cys-Pro-Leu Gly Amide
Cys-Tyr-Ile-Ser-Asn-Cys-Pro-Ile-Gly Amide
DAGO (D-Ala2, N-Me-Phe4-Gly5-ol-Enkephalin)
Dalargin
Decorin
Delta Sleep Inducing Peptide
Dermenkephalin
Dermorphin
Diabetes Associated Peptide Amide
Diazepam Binding Inhibitor and fragments
Diprotin A
Diprotin B
DNA Binding Peptide
Dynorphin and fragments
Echistatin
Elastatinal
Elastin Chemotactic protein and fragment
Eledoisin
Eledoisin-Related Peptide
Endothelin
alpha-Endorphin
beta-Endorphin and fragments
gamma-Endorphin
Endothelins
Enkephalin, Leucine and analogs
Enkephalinamide, Leucine and analogs
Enkephalin, Methionine and analogs
Enkephalinamide, Methionine and analogs
Enzyme Inhibitors
Eosinophilotactic Tetrapeptides
Epiamastatin
Epibestatin
Epidermal Growth Factor
Epidermal Mitosis Inhibiting Pentapeptide
Experimental Allergic Encephalogenic Peptide
Erythropoietin fragment 1–26
Fibrinogen-Binding Inhibitor Peptide
Fibrinogen Related Peptide
Fibrinogen A and analogs
Fibrinogen B and analogs
Fibroblast Growth Factor, Acidic fragment 1–11
Fibroblast Growth Factor, Basic fragment 1–24
Fibronectin-Binding Protein Peptide D3
Fibronectin fragments and analogs
Fibronectin Related Peptide
Fibronectin Pepsin (e.g. 50K)
Fibronectin Chymotrypsin (e.g. 40K, 45K, 120K)
Fibronectin Trypsin (e.g. 30K, 60 K)
N-FMOC-val-Gly-Gly-O-t-Butyl-Tyr-Gly-O-t-Butyl-Tyr-Gly-Ala-Ne-CBZ-Lys
N-Formyl-Met-Leu-Phe Formyl-Peptides
Foroxymithine
FTS (Serum Thymic Factor)
Galanin Message Associated Peptide and fragments
Galanin
Gastric Inhibitory Polypeptide
Gastrin I and fragments
Gastrin I, Big
Gastrin II
Pentagastrin
Gastrin Releasing Peptide
Gastrin-Tetrapeptide Amide
Gastrointestinal Peptides
Gilodeliquescin
Gin-Ala-Thr-Val-Gly-Asp-Ile-Asn-Thr-Glu-Arg-Pro-Gly-Met-Leu-Asp-Phe-Thr-Gly-Lys
Gln-AJa-Thr-Val-Gly-Asp-Val-Asn-Thr-Asp-Arg-Pro-Gly-Leu-Leu-Asp-Leu-Lys
Gln-Arg-Arg-Gln-Arg-Lys-Ser-Arg-Arg-Thr-Ile
Gln-Lys-Arg-Pro-Ser-Gln-Arg-Ser-Lys-Tyr-Leu
Glu-Ala-Glu
Glu-Ala-Glu-Asn
Glucagon
Glucagon(1–37)
Glucagon-Like Peptide I and fragments
Glu-Leu-Ala-Gly-Ala-Pro-Pro-Glu-Pro-Ala
Glutathione and analogs
Gly-Arg-Ala-Asp-Ser-Pro
Gly-Arg-Ada-Asp-Ser-Pro-Lys
Gly-Arg-Gly-Asp
Gly-Arg-Gly-Asp-Asn-Pro
Gly-Arg-Gly-Asp-Ser
Gly-Arg-Gly-Asp-Ser-Pro
Gly-Arg-Gly-Asp-Ser-Pro-Lys
Gly-Arg-Gly-Asp-Thr-Pro
Gly-Arg-Gly-Leu-Ser-Leu-Ser-Arg
Gly-Arg-Tyr-Asp-Ser
Gly-Gln
Gly-Glu-Gln-Arg-Lys-Asp-Val-Tyr-Val-Gin-Leu-Tyr-Leu
Gly-Gly-Arg
Gly-Gly-His
Gly-Gly-Tyr-Arg
Gly-His-Arg-Pro
Gly-His-Lys
Gly-Leu-Met Amide
Gly-Pen-Gly-Arg-Gly-Asp-Ser-Pro-Cys-Ala(Pen2, Cys9 cyclic)
Gly-Phe-Asp-Leu-Asn-Gly-Gly-Gly-Val-Gly
Gly-Pro-Arg
Gly-Pro-Arg-Pro
Gly-Pro-Gly-Gly
Granuliberin R
Granulocyte Macrophage-Colony Stimulating Factor
GRF 1–40, Human
Growth Hormone Release Inhibiting Factor
Growth Hormone Releasing Factor and fragments
H-142
Helodermin
Hepatitis A viral proteins and peptides
Hepatitis B Virus Pre-S Region (120–145)
Hepatitis C Viral proteins and peptides
Herpes Virus Ribonucleotide Reductase Inhibitors
Heterotypic Adhesion Receptor
Hirudin and fragments
His-Asp-Met-Asn-Lys-Val-Leu-Asp-Leu
His-Leu-Gly-Leu-Ala-Arg
His-Lys-Ala-Arg-Val-Leu-p-Nitro-Phe-Glu-Ala-Nle-Ser Amide
D-His-Pro-Phe-His-Leu-ph-[CH$_2$NH]-Leu-Val-Tyr
Histones
HIV Envelope Protein (gp41) fragment 579–601
HIV Envelope Protein (gp120) fragments
HIV Protease Inhibitor
HIV Substrate, III
HIV viral protein and peptides
Histone H2A fragment 86–120
Hydra Peptide and fragments
Hypercalcemia Malignancy Factor –40
Hypertrehalosaemic Neuropeptide
Iberiotoxin
Ile-Pro-Ile
Ile-Val-Pro-Phe-Leu-Gly-Pro-Leu-Leu-Gly Leu-Leu-Thr Amide
Immunostimulating Peptides
Inhibin, alpha subunit, fragment 1–32
Insulin Chain A, oxidized
Insulin Chain B, oxidized
Insulin Chain B fragment 22–30
Insulin Chain C
Insulin-Like Growth Factor I
Insulin-Like Growth Factor II
Integrin (e.g. alpha 4, alpha V beta 5 alpha2, alpha3, alpha 5, alpha V, beta 1, beta 2, beta 4)
Interleukin 1B fragment (163–171)
Interleukin-2 Receptor C-Terminal Sequence
Interleukin (e.g. 1 alpha, 2, 6, gamma)
Isotocin
Kallidin
Kallikrein Inhibitor
Kassinin
Katacalcin and analogs
Kemptide and analogs
Kentsin
Kinetensin
Kyotorphin and analogs
Laminin and fragments (929–933)
Leu-Arg-Arg-Ala-Ser-Leu-Gly
Leu-Arg-Arg-Ala-Hse-Leu-Gly
Leu-Arg-Arg-Trp-Ser-Leu-Gly
Leucokinins
Leucopyrokinin and fragments
Leu-Leu Methyl Ester
Leu-Lys-Lys-Phe-Asn-Ala-Arg-Arg-Lys-Leu-Lys-Gly-Ala-Ile-Leu-Thr-Met-Leu-Ala Leu-Pro-Pro-Ser-Arg
Leu-Ser-(pNO2)-Phe-Nle-Ala-Leu Methyl Ester
Leupeptin
LH-RH (Luteinizing Hormone Releasing Hormone) and analogs
beta-Lipotropin and fragments
Litorin
Lys-Arg-Pro-Pro-Gly-Phe-Ser-Pro-Phe-Arg
Lys-Ala-Arg-Val-Nle-p-Nitro-Phe-Glu-Ala-Nle Amide
Lys-Arg-Thr-Leu-Arg-Arg
Lys-Cys-Thr-Cys-Cys-Ala
Lys-Glu-Glu-Ala-Glu
Lys-His-Gly Amide
Lys-Lys-Arg-Ala-Ala-Arg-Ala-Thr-Ser-Amide
Lys-Lys-Asp-Ser-Gly-Pro-Tyr
Lys-Lys-Gly-Glu
Lys-Phe-Ile-Gly-Leu-Met Amide
Lys-Pro-Pro-Thr-Pro-Pro-Pro-Glu-Pro-Glu-Thr
Lys-Trp-Lys
D-Lys-Tyr-D-Trp-D-Trp-Phe
D-Magainin II Amide
Magainin I
Magainin II
Manning Compound
Manning-Binding Protein
Mast Cell Degranulating Peptide
Mast Cell Degranulating Peptide HR1
Mast Cell Degranulating Peptide HR2
Mastoparan
Alpha1-Mating Factor
MCD Peptide
MB-35
Alpha-Melanocyte Stimulating Hormone and analogs
Beta-Melanocyte Stimulating Hormone
Delta-Melanocyte Stimulating Hormone
Melittin
Merosin
Met-Asn-Tyr-Leu-Ala-Phe-Pro-Arg-Met Amide
Met-Gln-Met-Lys-Lys-Val-Leu-Asp-Ser
Met-Gly-Trp-Asn-Ser-Thr-Thr-Phe-His-Gln-Thr-Leu-Gln-Asp-Pro-Arg-Val-Arg-Gly-Leu-Tyr-Phe-Pro-Ala-Gly-Gly
Met-Leu-Phe
Metorphamide
Molluscan Cardioexcitatory Peptide
Morphiceptin
Morphine Modulating Neuropeptide
Morphine Tolerance Peptide
Motilin
MSH
Muramyl Dipeptides
Beta-Naphthyl-D-Ala-Cys-Tyr-D-Trp-Lys-Val-Cys-Thr Amide
coendorphin
Beta-Neoendorphin
Alpha-Neurokinin
(Ala5, Beta-Ala8)-alpha-Neurokinin fragment 4–10
Neurokinin (e.g., A, Nle-10, B, MePhe7-B)
Neuromedins (e.g., B,C)
Neuropeptide K
Neuropeptide Y
Neurotensin and analogs
N-Nicotinoyl-Tyr-(Nalpha-CBZ-Arg)-Lys-His-Pro-Ile
Nle-Arg-Phe Amide
Nle-Sta-Ala-Sta
NeutrAvidin
Octadecaneuropeptide (e.g. 6, 7, 8)
Osteocalcin fragment 7–19
Osteocalcin fragment 45–49
Oxyntomodulin
Oxytocin and analogs
PACAP27 Amide
Pancreastatin and fragments
Pancreatic Polypeptide
Parathyroid Hormone and fragments
Pardaxin
Pentagastrin
Pepstatin A
Peptide II of T, wagleri Venom
Peptide T
Peptide YY
pGlu-Ala-Glu
pGlu-Ala-Lys-Ser-Glu-Gly-Gly-Ser-Asn
pGlu-Asn-Gly
pGlu-Asp-Pro-Phe-Leu-Arg-Phe Amide
pGlu-Gln-Arg-Leu-Gly-Asn-Gln-Trp-Ala-Val-Gly-His-Leu-Met Amide
pGlu-Gln-Asp-Tyr(SO3H)-Thr-Gly-Trp-Met-Asp-Phe Amide
pGlu-Glu-Asp-Ser-Gly
pGlu-Gly-Leu-Pro-Pro-Arg-Pro-Lys-Ile-Pro-Pro
pGlu-Gly-Leu-Pro-Pro-Gly-Pro-Pro-Ile-Pro-Pro
pGlu-His-Gly
pGlu-His-Gly Amide
pGlu-His-Pro
pGlu-His-Pro Amide
pGlu-His-Pro-Gly
pGlu-His-Trp-Ser-Tyr-Gly-Leu-Arg-Pro-Gly Amide
pGlu-Leu-Tyr-Glu-Asn-Lys-Pro-Arg-Arg-Pro-Tyr-Ile-Leu
pGlu-Lys-Arg-Pro-Ser-Gln-Arg-Ser-Lys-Tyr-Leu
pGlu-3-Methyl-His-Pro Amide
(pGlu4)-Myelin Basic Protein 4–14
pGlu-Ser-Leu-Arg-Trp Amide
pGlu-Thr-Ser-Phe-Thr-Pro-Arg-Leu Amide;
pGlu-Trp-Pro-Arg-Pro-Gln-Ile-Pro-Pro
pGlu-Val-Asn-Phe-Ser-Pro-Gly-Trp-Gly-Thr Amide
Paracelsin
Peptide 6a
[D-Ala1]-peptide T amide
Phe-Gly-Gly-Phe
Phe-Gly-Leu-Met Amide
Phe-Gly-Phe-Gly
Phe-Leu-Arg-Phe Amide Phe-Leu-Glu-Glu-Ile
Phe-Leu-Glu-Glu-Leu
Phe-Leu-Glu-Glu-Val
Phe-Leu-Phe-Gln-Pro-Gln-Arg-Phe Amide
Phe-Met-Arg-Phe Amide
Phe-Met-Arg-D-Phe Amide
Phe-Met-D-Arg-Phe Anude
Phe-D-Met-Arg-Phe Amide
D-Phe-Met-Arg-Phe Amide
Phe-Ser-Trp-Gly-Ala-Glu-Gly-Gln-Arg
PHI
Phosphoramidon
Phosphate Acceptor Peptides
(Val6, Ala7)-Kemptide
Physalaemin
Platelet Derived Growth Factor (AB-chain, heterodimer, AA homodimer, BB homodimer)
Platelet Membrane Glycoprotein IIB Peptide
Pre-Pro-Gonadotropin Releasing Hormone fragment 14–26
Pressinoic Acid
N-proCalcitonin 1–57
Proctolin
Prodynorphin 228–240
Proenkephalin
Pro-His-Pro-Phe-His-Phe-Phe-Val-Tyr-Lys
Pro-Leu-Gly Amide
Pro-Phe-Gly-Lys
Pro-Leu-Ser-Arg-Thr-Leu-Ser-Val-Ala-Ala-Lys-Lys
Prosomatostatin 1–32
PYY
Protected Marine Adhesive Peptide
Protein A
Protein G (binds to Fc region, specially of IgG1 subclass)
Protein Kinase C
Protein Kinase C Substrate
Protein Kinase Inhibitor
Pro-Thr-Pro-Ser Amide
PTH
PTH-Related Protein (1–40)
Ranatensin
Renin Inhibitors
Renin Substrate Tetradecapeptide
N-(alpha-Rhamnopyranosyloxyhydroxyphosphinyl)-Leu-Trp
Sarafotoxin
Schizophrenia Related Peptide
Secretin
Senktide
Ser-Asp-Gly-Arg-Gly
Ser-Gln-Asn-Phe-Phi(CH$_2$N)-Pro-Ile-Val-Gln
Ser-Gin-Asn-Tyr-Pro-Ile-Val
Ser-Ile-Gly- Ser-Leu-Ala-Lys
Ser-Phe-Leu-Leu-Arg-Asn-Pro-Asn-Asp-Lys-Tyr-Glu-Pro-Phe
Serglycin
Serum Thymic Factor and analogs
Sexual Agglutination Peptide
Sleep Inducing Peptide
Small Cardioactive Peptide B
Somatostatin and analogs
Speract
Streptavidin
Streptolysin
Substance P and analogs
SV40 Tumor Antigen C-Terminal Sequence
Syndyphalin
Syntide
Tenascin
Terlipressin
Thapsigargin
DL-Thiorphan
Thr-Lys-Pro-Arg
Thrombin Receptor Activator
Thr-Phe-Gln-Ala-Tyr-Pro-Leu-Arg-Glu-Ala
Thr-Pro-Arg-Lys
Thr-Ser-Lys
Thr-Thr-Tyr-Ala-Asp-Phe-Ile-Ala-Ser-Gly-Arg-Thr-Gly-Arg-Arg-Asn-Ala-Ile-His-Asp
Thr-Tyr-Ser
Thr-Val-Leu
Thrombospondin
Thymopoietin fragments
Thymosin
Thymosin fragments
Thyrocalcitonin
Thyrotropin Releasing Hormone and Related Peptides
Tocinoic Acid
Toxin, Snake
TP-5
Transforming Growth Factor-Alpha
TRH
Trp-Ala-Gly-Gly-Asp-Ala-Ser-Gly-Glu
D-Trp-Ala-Trp-D-Phe Amide
Trp-His-Trp-Leu-Gln-Leu
Trp-His-Trp-Leu-Gln-Leu-Lys-Pro-Gly-Gln-Pro-Met-Tyr
Trp-His-Trp-Leu-Ser-Phe-Ser-Lys-Gly-Glu-Pro-Met-Tyr
Trp-Met-Asp-Phe Amide
Trp-Nle-Arg-Phe Amide
Tuftsin and analogs
Tumor Necrosis factor (e.g. alpha) Tyr-Ala-Gly-Ala-Val-Val-Asn-Asp-Leu
Tyr-D-Ala-Phe-Asp-Val-Val-Gly Amide
Tyr-D-Ala-Phe-Glu-Val-Val-Gly Amide
Tyr-Gly-Ala-Val-Val-Asn-Asp-Leu
Tyrosine Protein Kinase Substrate
Tyr-D-Ala-Gly
Tyr-Gly-Gly
Tyr-D-Ala-Phe-Met Amide
Tyr-Arg
Tyr-Gly-Gly
Tyr-Gly-Gly-Phe-Leu
Tyr-Gly-Gly-Phe-Leu-Arg-Arg-Ile-Arg-Pro-Arg-Leu-Arg-Gly-Aminopentylamide Tyr-Gly-Gly-Phe-Met-Arg-Arg-Val
Tyr-Gly-Gly-Phe-Met-Arg-Arg-Val Amide
Tyr-Gly-Gly-Phe-Met-Arg-Gly-Leu
Tyr-Gly-D-Trp-Phe-D-Phe Amide
Tyr-Ile-Gly-Ser-Arg
Tyr-Phe-Met-Arg-Phe Amide
Tyr-Pro-Leu-Gly Amide
Tyr-Pro-Phe-Pro Amide
Tyr-Pro-Val-Pro Amide
Tyr-D-Ser-Gly-Phe-Leu-Thr
Tyr-D-Trp-Ala-Trp-D-Phe Amide
Tyr-D-Trp-Ala-Trp-D-Phe Methyl Amide
Urodilatin
Urotensin I
Urotensin II
Val-Ala-Ala-Phe
Val-Arg-Lys-Arg-Thr-Leu-Arg-Arg-Leu
Val-Glu-Glu-Ala-Glu
Val-Glu-Pro-Ile-Pro-Tyr
Val-Glu-Ser-Ser-Lys
Val-Gly-Asp-Glu
Val-Gly-Ser-Glu
Val-Gly-Val-Ala-Pro-Gly
Val-His-Leu-Thr-Pro
Val-His-Leu-Thr-Pro-Val-Glu-Lys
Val-Ile-His-Asn
Valosin
Val-Pro-Leu
Vasoactive Intestinal contractor
Vasoactive Intestinal Peptide and analogs
Vasopressin and analogs
Vasotocin
Versican
Vitronectin
Xenopsin
Yeast Alpha-Factor
Human Serum Albumin Glycoconjugates
Carboxyethylthioethyl 2-Acetamido-2-deoxy-3-O-Beta-D-galactopyranosyl-beta-D-glucopyranoside-HSA Conjugate
Carboxyethylthioethyl 2-Acetamido-2-deoxy-4-O-beta-D-galactopyranosyl-beta-D-glucopyranoside-HSA Conjugate
Carboxyethylthioethyl 2-Acetamido-4-O-(2-acetamido-2-deoxy-beta-D-glucopyranosyl-6-O-(alpha-L-fucopyranosyl))-2-deoxy-beta-D-glucopyranoside-HSA Conjugate
Carboxyethylthioethyl 4-O-alpha-D-Galactopyranosyl-beta-D-galactopyranoside-HSA Conjugate
Carboxyethylthioethyl 4-O-(4-O-(6-O-alpha-D-Glucopyranosyl-alpha-D-glucopyranosyl)-alpha-D-glucopyranosyl)-beta-D-glucopyranoside-HSA Conjugate
Free Oligosaccharides and Simple Derivatives
2-Acetamido-6-O-(2-acetamido-2-deoxy-beta-D-glucopyranosyl)-2-deoxy-D-glucopyranose
2-Acetamido-2-deoxy-3-O-beta-D-galactopyranosyl-D-galactopyranose
2-Acetamido-2-deoxy-4-O-(4-O-Beta-D-galatopyranosyl-beta-D-galactopyranosyl)-D-glucopyranose
2-Acetamido-2-deoxy-3-O-beta-D-galactopyranosyl-D-glucopyranose
2-Acetamido-2-deoxy-6-O-beta-D-galactopyranosyl-D-glucopyranose
6-O-(2-Acetamido-2-deoxy-4-O-(beta-D-galactopyranosyl)-beta-D-glucopyranosyl)-D-galactopyranose
6-O-(2-Acetamido-2-deoxy-beta-D-glucopyranosyl)-D-galactopyranose
4-O-(6-O-(2-Acetamido-2-deoxy-beta-D-glucopyranosyl)-beta-D-galactopyranosyl)-D-glucopyranose
N-Acetyllactosamine
Benzyl 2-Acetamido-6-O-(2-acetamido-2-deoxy-beta-D-glucopyranosyl)-2-deoxy-alpha-D-glucopyranoside
Benzyl 2-Acetamido-2-deoxy-3-O-beta-D-galactopyranosyl-alpha-D-galactopyranoside
Benzyl 2-Acetamido-2-deoxy-3-O-beta-D-galactopyranosyl-beta-D-glucopyranoside
Benzyl 4-O-beta-D-Galactopyranosyl-beta-D-glucopyranoside
n-Butyl 4-O-beta-D-Galactopyranosyl-beta-D-glucopyranoside
D-(+)-Cellobiose
D-(+)-Cellopentaose
D-(+)-Cellotetraose
D-(+)-Cellotriose
Digalacturonic acid
Ethyl 2-Acetamido-2-deoxy-4-O-(4-O-alpha-D-galactopyranosyl-beta-D-galactopyranosyl)-beta-D-glucopyranoside
Ethyl 4-O-beta-D-Galactopyranosyl-beta-D-glucopyranoside
2'-Fucosyllactose
3-Fucosyllactose
4-O-alpha-D-Galactopyranosyl-D-galactopyranose
6-O-beta-D-Galactopyranosyl-D-galactopyranose
4-O-(4-O-beta-D-Galactopyranosyl-beta-D-galactopyranosyl)-D-Glucopyranose
4-O-beta-D-Galactopyranosyl-D-mannopyranose
4-O-(4-O-(6-O-alpha-D-Glucopyranosyl-alpha-D-glucopyranosyl)alpha-D-glucopyranosyl)-D-glucopyranose
Lacto-N-tetraose
3-O-alpha-D-Mannopyranosyl-D-mannopyranose
Methyl 4-O-(3-O-(2-Acetamido-2-deoxy-4-O-beta-D-galactopyranosyl-beta-D-glucopyranosyl)-beta-D-galactopyranosyl)-beta-D-glucopyranoside
Methyl 3-O-(2-Acetamido-2-deoxy-beta-D-glucopyranosyl)-beta-D-galactopyranoside
Methyl 6-O-(2-Acetamido-2-deoxy-beta-D-glucopyranosyl)-alpha-D-mannopyranoside
Methyl 3,6-Di-O-(alpha-D-mannopyranosyl)-alpha-D-mannopyranoside
Methyl 3-O-beta-D-Galactopyranosyl-beta-D-galactopyranoside
4-O-(2-O-Methyl-beta-D-galactopyranosy)-D-glucopyranose
Methyl 4-O-beta-D-Galactopyranosyl-beta-D-glucopyranoside
Methyl 2-O-alpha-D-Mannopyranosyl-alpha-D-mannopyranoside
Methyl 3-O-alpha-D-Mannopyranosyl-alpha-D-mannopyranoside Methyl 4-O-alpha-D-Mannopyranosyl-alpha-D-mannopyranoside Methyl 6-O-alpha-D-Mannopyranosyl-alpha-D-mannopyranoside n-Propyl 4-O-beta-D-Galactopyranosyl-beta-D-glucopyranoside Trigalacturonic acid Activated Oligosaccharides Carbomethoxyethylthioethyl 2-Acetamido-2-deoxy-4-O-beta-D-galactopyranosyl-beta-D-glucopyranoside Carbomethoxyethylthioethyl 4-O-(4-O-(6-O-alpha-D-Glucopyranosyl-alpha-D-glucopyranosyl)-alpha-D-glucopyranosyl)-beta-D-glucopyranoside p-Nitrophenyl 2-Acetamido-2-deoxy-3-O-(2-acetamido-2-deoxy-beta-D-glucopyranosyl)-alpha-D-galactopyranoside p-Nitrophenyl 2-Acetamido-2-deoxy-3-O-(Beta-D-galactopyranosyl)-alpha-D-galactopyranoside p-Nitrophenyl 2-Acetamido-2-deoxy-3-O-beta-D-galactopyranosyl-beta-D-glucopyranoside p-Nitrophenyl 6-O-beta-D-galactopyranosyl-beta-D-galactopyranoside p-Nitrophenyl alpha-D-Maltopentaoside Neo-glycolipids Octadecylthioethyl 4-O-alpha-D-Galactopyranosyl-beta-D-galactopyranoside Octadecylthioethyl 4-O-(4-O-(6-O-alpha-D-Glucopyranosyl-alpha-D-glucopyranosyl)-alpha-D-glucopyranosyl)-beta-D-glucopyranoside Coagulation Proteins and Various Factors, and Their Fragments, Inhibitors, Receptors to Which They Bind, or Genes and Information Molecules from Which They May be Derived Acutase; Agkistrodon contortrix Thrombin-like Enzyme; Ancrod; α2-Antiplasmin; Antithrombin III; Atroxin; Coagulation Factors; Coagulation factor Inhibitors; Crotalase; Ecarin; Factor I, II, III, IV, V; Factor V Activating Enzyme; Factor VI, VII; VIII; Von-Willebrand Factor; Factor IX; Factor X; Factor X, Activiated (Xa) Factor X Activating Enzyme; Factor XI, XII, XIII; Fibrin; Fibrin/Fibrinogen Degradation Products; Fibrinogen; Fibrinolytic proteins; Heparin; Hirudin; Kallikrein; Plasmin; Plasminogen; Plasminogen Lysine Binding Sites; Platelet Factor 4; Platelet Aggregation Reagent; Brain Cephalin; Snake venoms; Streptokinase; Thrombins; Thromboplastin; Thromboplastin with Calcium; Tissue Plasminogen Activator; Urokinase Agents and Drugs Used to Treat or Prevent HIV Infection Alpha interferon, Interleukin-2, Amphotericin B, Amphotericin B Methyl Est; Ampligen (polyI-polyC; C12U); AS-101 (ammonium trichloro(dioxyethylene-O-O' tellurate); CD8+ lymphycyte proteins; HIV vital proteins, cell receptor anagonists, cell receptor binding proteins; azidothymidine and analogs or conjugates; Azidouridine (including analogs or conjugates); beta interferon; Carbovir; Carrisyn; Colchicine; Colony Stimulating Factors; Compound Q; D4T (2',3'-didehydro-3'-dideoxythymidine); DTC (Imuthiol); Dextran Sulfate; Dideoxycytidine; Dideoxyinosine; DHEA (dehydroepiandro-sterone); Doxorubicin; gamma globulin; HIV-immunogen; Hypericin; tyrosine-glycine dipeptide; tyrosine-glycine-glycine tripeptide; Isoprinosine; Lentinan (beta-(1-3)-glucan); Lipid compounds, e.g. AL-721 or EL-721 and like products; Peptide T; Polio Vaccine proteins; soluble CD4; CD4-linked toxins; Ribavirin; SMS 201–995 (a long-acting analog of somatostatin); Thymic Humoral Factor; Thymopentin; Tumor Necrosis Factor; ketoconazole; fluconazole; Eflornithine; Spiramycin; Ganciclovir (DHPG); Foscarnet; Acyclovir; Vibaradine; Pyrimethamine; sulfadiazine; TMP/SMX; Amikacin; Ansamycin; Ciprofloxacin; Clofazamine; Cycloserine; Imipenum; Ethambutol; Isoniazide; Rifampin; Streptomycin; sulfa based antibiotics; pentamidine; Dapsone/trimethoprim; steroids; Trimetrexate with Leukovorin; Clindamycin; primaquin; Dapasone; Spiramycin; piritrexim Adjuvant Peptides N-acetylmuramyl-L-alanyl-D-isoglutamine N-acetylmuramyl-D-alanyl-D-isoglutamine N-acetylmuramyl-L-alanyl-L-isoglutamine N-acetylmuramyl-L-alanyl-D-isoglutamine-6-O-stearoyl N-acetyl-glucosaminyl-beta(1–4)-N-acetylmuramyl-L-alanyl-D-isoglutamine Components of Freund's Complete Adjuvant Components of Freund's Incomplete Adjuvant Dimethyldioctyldecyl Ammonium Bromide Lipoproteins and Related Enzymes Apolipoprotein A (I and II), B, CIII, CII, CI, E High Density Lipoprotein Low Density Lipoprotein Very Low Density Lipoprotein Lipoprotein Lipase Lipoteichoic Acid Lipoxidase Diaphorase Lipoxin A4, B4

Lipoxygenase

Prostaglandan Synthetase

Chelating Agents

Iminodiacetic Acid (e.g., dimethyl-ida, paraisopropyl-ida, parabutyl-ida, diisopropyl-ida, diethyl-ida)

EDTA (Ethylenediaminetetraacetic acid)

NTA (Nitriloacetic acid)

TPP (Tripolyphosphate

Cysteine

DEDTC (Diethyldithiocarbamate)

Citric acid

Tartaric acid

Penicillamine

EGTA

Caged Calcium Chelators

NITR5, NITR7, DM-nitrophen, NITRS/AM; Ammonium N-nitrosophenyl-hydroxylamine; Ammonium purpurate; alpha-Benzoin oxime; N, N-Bis-(hydroxyethyl)-glycine; 2,3-butane-dione dioxime; Trans-1,2-Diaminocyclohexanetetra-acetic acid (CDTA); Diethylenetriaminopenta-acetic acid (DTPA); 4,5-Dihydroxybenzene-1,3-disulphonic acid; 2,3-Dimercapto-1-Propanol; Diphenylthio-carbazone; 2,2'-Dipyridyl; 3,6-Disulpho-1,8-dihydroxy-naphthalene; Dithiooxamide; Eriochrome Black T; Ethylenediamine; Ethylenediaminetetraacetic acid (EDTA); (Ethylene-dioxy)-diethylenedinitrilo-tetraacetic acid (EGTA); o-Hydroxybenzaldehyde oxime; N-(2'-Hydroxyethyl)iminodiacetic acid (HIMDA); 8-Hydroxy-quinoline; 8-Hydroxyquinoline-5-sulphonic acid; 4-Methyl-1,2-dimercapto-benzene; Nitrilotriacetic acid (NTA); 5-Nitro-1,10-phenanthroline; 1,10-Phenanthroline; Potassium ethyl xanthate; Salicylic acid; sodium diethyldithiocarbamate; 2-Thenoyl-2-furoylmethane; Thenoyl-trifluoroacetone; Thiourea; Triethylenetetramine Deferoxamine mesylate Edetate Calcium disodium meso 2,3-dimercapto succinic acid Penicillamine Trientine Chelators Specially Useful in Chelating Tc99m:

A thiolactone diaminedithiol bifunctional chelating agent p-carboxyethylphenylglyoxal-di-N-methylthioxemicrobazone A diamide dimercaptide chelating agent A hydroxy compound (e.g. cyclohexanol) attached to cysteine Bisthio semicarbazones Cyclan Diamido dithio ligands Radionuclides Indium 111

Thallium 201

Technetium 99m

Other Compounds and Chelates Suitable for MRI Imaging

Gadolinium, Cadmium, Strontium, Chromium; ferrous gluconate; manganese; nickel, piperidine and pyrrolidine NSFR derivatives, ferric ammonium citrate Reagents That Can be Used to Provide Spacer Arms for Bioreactive Molecules to Extend Beyond the Immediate Surface of the Particles Biocytin Biocytin hydrazide p-Aminobenzoyl Biocytin Enzymes Alteplase; Anistreplase; Adenosine Deaminase; Amylase; Angiotensin I, II, III; Calmodulin; Carboxypeptidase; Catalase; Cellulase; Cholesterol oxidase; Cholinesterase; Chymotrypsin; Collagenase; Complement cascade proteins; Creatine phosphokinase; Deoxyribonuclease I, II; Dipeptidyl peptidase; DNA polymerase; Endoproteinase; Endonucleases; Esterases; beta-Galacatosidase; Galactose oxidase; Galactose dehydrogenase; Glucose dehydrogenase; Glucose oxidase; Glucose-6-phosphate dehydrogenase; Glucuronidase/Aryl sulfatase; Glutamate-oxaloacetate transaminase; Glutamate-pyruvate transaminase; Glutathione reductase; Glutathione peroxidase; Glycopeptidase; Hementin; Hemoglobin; Hexokinase; Hyaluronidase; Lactate dehydrogenase; Lactoperoxidase; Lactamase; Lipase; Myokinase; Neuraminidase; Nicotinamide-adenine Dinucleotide kinase; Nicotinamide-adenine Dinucleotide oxidase; Nuclease; Nucleosidase; Papain; Peroxidase; Phenylalanine dehydrogenase; phosphatase (acid or alkaline); Phosphodiesterase; Phospholipase (A2, C, D); Plasmin; Proteases; Protein Kinase C; Proteinase K; Renin; Reverse transcriptase; Ribonuclease (A, T1, T2, U2); RNA polymerase; Sialyltransferase; Streptokinase; Subtilisin A; Superoxide dismutase; Terminal transferase; Urease; Urokinase Nucleotides and Fragments Thereof anti-sense (DNA or RNA against RNA or DNA, single or double stranded), cloning vectors, coliphage DNA, lambda phage DNA, M13 DNA, Adenovirus DNA, phi-X 174 phage DNA, Simian virus DNA, cytomegalovirus DNA, Epstein-Bart Virus genes, Herpes Simplex genes, ribosomal RNA, human DNA and RNA; Genes coding for ribozymes; genes coding for antibiotics (e.g., ampicillin, chloramphenicol, cycloserine, gentamycin, kanamycin, kasugamycin, nalidixic acid, rifampicin, spectinomycin, streptomycin, tetracycline)

Platelet Related Proteins and Enzymes

Platelet factor 4; 1–3-Dioxolane; 1-O-Hexadecyl-2-acetyl-sn-glucero-3-phospho-(N,N,N-trimethyl)-hexanolamine; Platelet activating factors (e.g., 1-O-hexadecyl-2-acetyl-sn-glycero-3-phosphocholine; 3-O-hexadecyl-2-acetyl-sn-glycero-1-phosphocholine; 1-O-hexadecyl-sn-glycero-3-phosphocholine; 1-O-hexadecyl-2-N-methylcarbamyl-sn-glycero-3-phosphocholine; 1-O-hexadecyl-2-thioacetyl-2-deoxy-sn-glycero-3-phosphocholine; 1-O-hexadecyl-2-acetyl-sn-glycero-3-phospho(N-methylpyrrolidino)-ethanolamine); Platelet activating factor 18; 18:1; Lyso-platelet activating factor 18; platelet activating factor-16; Enantic-platelet activating factor-16; Lyso-platelet activating factor-16; trans-2,5-bis-(3,4,5-trimethoxyphenyl); 1-O-Hexadecyl-2-acetyl-sn-glycero-3-phospho(N,N,N-trimethyl)-hexanolamine.

Other Compounds

Protein A,B,C,G,S; Ricin A; Proadifen (SKF-525A)1 Taxol; Thiolytes; Thiostrepton; Thrombin Thrombocytin; beta-Thromboglobulin; Thrombospondin; Transferrin (apo-, partial iron, holo); Tumor Necrosis factor; Vitronectin, Forskolin, Integrins; caged compounds (caged ATP, caged INsP3, caged cAMP, caged cGMP, caged GTP, caged carbamoyl chorine); Mezerein; Plasminogen; Aminocaproic acid; desmopressin acetate; Activase RGD-containing Peptides Gly-Arg-Gly-Asp-Ser-Pro Gly-Arg-Gly-Asp-Thr-Pro Gly-Arg-Gly-Asp-D-Ser-Pro Gly-D-Arg-Gly-Asp-Ser-Pro Gly-Arg-Gly-Glu-Ser-Pro (inactive control peptide)

Gly-Arg-Gly-Asp-Asn-Pro n-Methyl-Gly-Arg-Gly-Asp-Ser-Pro

Arg-Gly-Asp-Ser

Gly-Arg-Gly-Asp-Ser

Gly-Arg-Gly-Asp-Ser-Pro-Cys

Gly-Arg-Gly-Asp-Ser-Pro-Lys

Gly-Arg-Gly-Asp-Ser-Pro-Ala-Ser-Ser-Lys (Gly-Pen-Gly-Arg-Gly-Asp-Ser-Pro-Cys-Ala [cyclical])

The foregoing is offered primarily for purposes of illustration. It will be readily apparent to those skilled in the art that the materials, proportions, methods of preparation and formulation and other parameters of the various systems described herein may be further modified or substituted in various ways without departing from the spirit and scope of the invention.

What is claimed is:

1. A suspension of particles of non-crosslinked and non-denatured albumin in a first aqueous medium, said particles being monodisperse in said suspension, and having a size range of from about 50 to about 5000 nanometers in diameter, said particles further containing hemoglobin in an amount sufficient to prevent said particles from dissolving upon dilution of said suspension with a second aqueous medium which is alcohol-free, to a volume increase of at least about 50%.

2. A suspension of particles in accordance with claim 1 in which said particles comprise at least about 3 g per liter of said suspension.

3. A suspension of particles in accordance with claim 1 in which said particles comprise from about 5 to about 50 g per liter of said suspension.

4. A suspension of particles in accordance with claim 1 in which said amount of hemoglobin is at least about 1% by weight relative to the total of said albumin and said hemoglobin.

5. A suspension of particles in accordance with claim 1 in which said amount of hemoglobin is from about 1% to about 70% by weight relative to the total of said albumin and said hemoglobin.

6. A suspension of particles in accordance with claim 1 in which said amount of hemoglobin is from about 1% to about 30% by weight relative to the total of said albumin and said hemoglobin.

7. A suspension of particles in accordance with claim 1 in which said amount of hemoglobin is from about 1% to about 10% by weight relative to the total of said albumin and said hemoglobin.

8. A suspension of particles in accordance with claim 1 in which said first aqueous medium further includes an anionic water-soluble surfactant.

9. A suspension of particles in accordance with claim 8 in which said anionic water-soluble surfactant is a member selected from the group consisting of sodium and potassium alcohol sulfates.

10. A suspension of particles in accordance with claim 8 in which said anionic water-soluble surfactant is a member selected from the group consisting of sodium lauryl sulfate and sodium tetradecylsulfate.

11. A suspension of particles in accordance with claim 8 in which said anionic water-soluble surfactant is included at a concentration of at least about 0.1 g per liter of said suspension.

12. A suspension of particles in accordance with claim 8 in which said anionic water-soluble surfactant is included at a concentration of from about 0.5 g to about 5 g per liter of said suspension, and said particles comprise at least about 15 g per liter of said suspension.

13. A suspension of particles in accordance with claim 8 in which said anionic water-soluble surfactant is a member selected from the group consisting of sodium lauryl sulfate and sodium tetradecylsulfate at a concentration of from about 0.5 g to about 5 g per liter of said suspension, and said particles comprise at least about 15 g per liter of said suspension.

14. A suspension of particles in accordance with claim 1 in which said first aqueous medium further includes a lower alkyl alcohol.

15. A suspension of particles in accordance with claim 14 in which said lower alkyl alcohol constitutes from about 10% to about 80% by volume of said first aqueous medium.

16. A suspension of particles in accordance with claim 14 in which said lower alkyl alcohol is a member selected from the group consisting of methanol, ethanol, n-propanol, isopropanol and n-butanol.

17. A suspension of particles in accordance with claim 14 in which said lower alkyl alcohol is a member selected from the group consisting of ethanol and n-butanol.

18. A suspension of particles in accordance with claim 1 in which said albumin is human serum albumin.

19. A suspension of particles in accordance with claim 1 in which said hemoglobin is human hemoglobin.

20. A suspension of particles in accordance with claim 1, said particles further including biologically active macromolecules other than albumin or hemoglobin immobilized on the exterior of said particles.

21. A suspension of particles in accordance with claim 20 in which said biologically active macromolecules are members selected from the group consisting of proteins, immunoglobulins and nucleic acids.

22. A suspension of particles in accordance with claim 1, said particles further including a member selected from the group consisting of fibrinogen and arginine-glycine-aspartic acid immobilized on the exterior of said particles.

23. A suspension of particles in accordance with claim 1 in which said particles further comprise a biologically active substance other than albumin or hemoglobin distributed substantially homogeneously within said particles.

24. A suspension of particles in accordance with claim 23 in which said biologically active substance is a member selected from the group consisting of enzymes, amino acids, peptides, nucleic acids and nonmacromolecular therapeutic drugs.

25. A suspension of particles in accordance with claim 1, said particles further including biologically active macromolecules other than albumin or hemoglobin immobilized on the exterior of said particles and distributed substantially homogeneously within said particles.

26. A suspension of particles in accordance with claim 1 in which said particles further comprise technetium distributed within said particles.

* * * * *